(12) United States Patent
Cui et al.

(10) Patent No.: US 9,724,506 B2
(45) Date of Patent: Aug. 8, 2017

(54) NANOPILLAR ELECTRODE DEVICES AND METHODS OF RECORDING ACTION POTENTIALS

(71) Applicant: The Board of Trustees of the Leland Stanford Junior University, Palo Alto, CA (US)

(72) Inventors: Bianxiao Cui, Stanford, CA (US); Yi Cui, Stanford, CA (US); Ziliang Lin, Stanford, CA (US); Chong Xie, Cambridge, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 449 days.

(21) Appl. No.: 14/168,906

(22) Filed: Jan. 30, 2014

(65) Prior Publication Data

US 2014/0222123 A1    Aug. 7, 2014

Related U.S. Application Data

(60) Provisional application No. 61/761,570, filed on Feb. 6, 2013.

(51) Int. Cl.
*A61N 1/04* (2006.01)

(52) U.S. Cl.
CPC ......... *A61N 1/0472* (2013.01); *A61N 1/0412* (2013.01); *Y10T 29/49147* (2015.01)

(58) Field of Classification Search
CPC ................ A61N 1/0472; A61N 1/0412; Y10T 29/49147; C12M 35/02
See application file for complete search history.

(56) References Cited

U.S. PATENT DOCUMENTS

2003/0009103 A1*  1/2003  Yuste ............... A61B 5/0059
                                                  600/476
2006/0121446 A1*  6/2006  Abassi .............. C12M 35/02
                                                  435/4

(Continued)

FOREIGN PATENT DOCUMENTS

WO    WO 2012050876 A2 *  4/2012  .......... A61B 5/6877

OTHER PUBLICATIONS

Xie; et al., "Intracellular recording of action potentials by nanopillar electroporation", Nature Nanotechnology (Feb. 2012), 7:185-90.*

(Continued)

*Primary Examiner* — Sean E Conley
*Assistant Examiner* — Matthew Krcha
(74) *Attorney, Agent, or Firm* — Le Tian; Tian IP & Technology, LLC.

(57) ABSTRACT

This disclosure provide a nanopillar electrode device, comprising a substrate patterned with a plurality of metal pads. The device may further comprise a plurality of nanopillars electrode arrays, wherein each nanopillar electrode array is attached to the substrate above a metal pad and electrically connected to the pad. The device may further comprise and a chamber surrounding the nanopillar electrodes, which can be used for culturing cells of interest for recording action potentials. The nanopillar electrode device may be configured to apply a voltage through the nanopillar electrodes from a voltage source. Nanopillar electroporation may be used to increase the permeability of cell membranes to allow intracellular recording. Also provided are methods of device fabrication, and methods of use.

5 Claims, 16 Drawing Sheets

(56) References Cited

U.S. PATENT DOCUMENTS

2010/0035322 A1* 2/2010 Raffa ............... A61K 41/0047
435/173.7
2013/0284612 A1 10/2013 Park et al.

OTHER PUBLICATIONS

Hai; et al., "Long-Term, Multisite, Parallel, In-Cell Recording and Stimulation by an Array of Extracellular Microelectrodes", J. Neurophysiol. (Apr. 2010), 104(1): 559-568.*

Hai; et al., "Changing gears from chemical adhesion of cells to flat substrata toward engulfment of micro-protrusions by active mechanisms", J. Neural Eng. (Nov. 2009) 6(6): 066009-12.*

Hai; et al., "On-chip electroporation, membrane repair dynamics and transient in-cell recordings by arrays of gold mushroom-shaped microelectrodes", Lab on a Chip. (Apr. 2012), 12: 2865-2873.*

Hai; et al., "Spine-shaped gold protrusions improve the adherence and electrical coupling of neurons with the surface of microelectronic devices", J. R. Soc. Interface (May 2009), 6: 1153-1165.*

Hai; et al., "In-cell recordings by extracellular microelectrodes", Nature Methods (Jan. 2010), 7(3): 200-203.*

Cogan, "Neural stimulation and recording electrodes", Annu. Rev. Biomed. Eng. (Apr. 2008), 10;275-309.

Duan; et al., "Intracellular recordings of action potential by an extracellular nanoscale field-effect transistor", Nat. Nanotechnol. (Dec. 2011), 7(3):174-9.

Mafakheri; et al., "Synthesis of Iridium Oxide Nanotubes by Electrodeposition into Polycarbonate Template: Fabrication of Chromium(III) and Arsenic(III) Electrochemical Sensor", Electroanalysis (Jul. 2011), 23(10):2429-37.

Meyer; et al., "Electrodeposited iridium oxide for neural simulation and recording electrodes.", IEEE Trans. Neural Sys. Rehabil. Eng. (Mar. 2001), 9(1):2-11.

Robinson; et al., "Vertical nanowire electrode arrays as a scalable platform for intracellular interfacing to neuronal circuits", Nat. Nanotechnol. (Jan. 2012), 7(3):180-4.

Tian; et al., "Three-Dimensional, Flexible Nanoscale Field-Effect Transistors as Localized Bioprobes", Science (Aug. 2010), 329(5993):830-4.

Wang; et al., "Neural Stimulation with a Carbon Nanotube Microelectrode Array", Nano. Lett. (Sep. 2006), 6 (9):2043-8.

* cited by examiner

NANOPILLAR ELECTRODE DEVICES AND METHODS OF RECORDING ACTION POTENTIALS

STATEMENT REGARDING FEDERALLY SPONSORED RESEARCH OR DEVELOPMENT

This invention was made with Government support under contract 1055112 awarded by the National Science Foundation. The Government has certain rights in this invention.

BACKGROUND

Action potentials play a central role in the nervous system and in many cellular processes, notably those involving ion channels. The accurate measurement of action potentials requires efficient coupling between the cell membrane and the measuring electrodes. Extracellular recording methods may be limited by signal strength and signal-to-noise ratio. Intracellular recording methods such as patch clamping involve measuring the voltage or current across the cell membrane by accessing the cell interior with an electrode, allowing both the amplitude and shape of the action potentials to be recorded faithfully with high signal-to-noise ratios. The invasiveness of traditional intracellular recording techniques, such as patch clamping, may reduce the duration and scalability of measurements.

SUMMARY

A nanopillar electrode device and method of recording action potentials with such devices are provided herein. The nanopillar electrode devices can be used to record both extracellular and intracellular action potentials of cells. In certain aspects, nanopillar electroporation may be used to increase the permeability of cell membranes to allow intracellular recording. The methods of certain embodiments described herein may be used, for example, for measuring membrane potentials from excitable cells (e.g., neurons, cardiomyocytes, muscle fibers, and endocrine cells), and may be useful in distinguishing cell types based on the shapes of their action potentials, detecting changes in action potentials induced by drugs that target ion channels, and monitoring differentiation of stem cells into various cell types (e.g., excitable cells).

In one aspect, a nanopillar electrode device may comprise (a) a substrate patterned with a plurality of metal pads; (b) a plurality of nanopillars electrode arrays, wherein each nanopillar electrode array is attached to the substrate above a metal pad and electrically connected to the pad; and (c) a chamber surrounding the nanopillar electrodes, which can be used for culturing cells of interest for recording action potentials. The device may further comprise one or more recording amplifiers, wherein each recording amplifier is electrically connected to a metal pad by an electrical lead.

Exemplary devices are described in Example 1 and depicted in FIG. 1a-1f, FIG. 6a-6d, and FIG. 10. In certain embodiments, the footprint of the nanopillar electrode array on each pad may be less than or equal to 5×5 $\mu m^2$. The metal pads may be electrically insulated with a $Si_3N_4/SiO_2$ layer. The substrate may be composed of a transparent material, such as quartz or glass to allow visualization of cells. In certain embodiments, the plurality of metal pads may be arranged in a three-by-three array of metal pads or a four-by-four array of metal pads, wherein each metal pad comprises and array of nanopillar electrodes. In certain embodiments, the number of nanopillar electrodes per pad ranges from 1 to 20 per pad, including any number of nanopillar electrodes within this range, such as 1, 2, 3, 4, 5, 6, 7, 8, 9, 10, 11, 12, 13, 14, 15, 16, 17, 18, 19, or 20 nanopillar electrodes per pad. The nanopillar electrodes may comprise a biocompatible metal, such as, but not limited to one or more of platinum, titanium, silver, gold, a metal alloy comprising at least one or more of platinum, titanium, silver, and gold, and oxides thereof. In certain embodiments, the nanopillar electrodes may comprise one or more of iridium, titanium, and an oxide thereof. In certain embodiments, the nanopillar electrodes may be hollow. In certain embodiments, each nanopillar electrode may be 1-2 $\mu m$ long and 150-200 nm in diameter. In certain embodiments, the device may be configured to apply a voltage through the nanopillar electrodes In another aspect, a method for measuring action potentials from a cell with a nanopillar electrode device described herein may comprise: (a) providing a nanopillar electrode array in contact with a portion of the cell membrane of the cell; (b) electroporating the cell to increase the permeability of the cell membrane; and (c) recording one or more action potentials.

The nanopillar electrode device may comprise a plurality of electrodes capable of recording action potentials from a plurality of cells simultaneously, wherein each electrode is in contact with a portion of the cell membrane of a different cell. Alternatively, the nanopillar electrode device may comprise a plurality of electrodes, wherein each electrode is in contact with different portions of the cell membrane of the same cell. Action potentials may be recorded from various types of excitable cells, including, but not limited to neurons, muscle cells, and endocrine cells. In certain embodiments, action potentials are recorded from cardiomyocytes. Action potentials may be recorded from a plurality of cells simultaneously. During measurements of action potentials, cells may be mechanically pinned down with a nanopillar electrode to prevent cell migration, if desired. In certain aspects, the electroporation may be performed with biphasic pulses at 2.5 V for 200 microseconds. The electroporation may be repeated for 20 pulses over a period of 1 second. In another aspect, a method of screening an agent for its effect on cellular action potentials with a nanopillar electrode device may comprise: (a) measuring action potentials from a cell before and after treatment of the cell with the agent; and (b) comparing action potentials before and after treatment of the cell with the agent to detect any changes in the action potentials resulting from treatment of the cell with the agent. In certain embodiments, the agent is an ion channel blocker, a ligand for an ion channel or a receptor, a hormone, or a second messenger. Changes in the shape, duration, or frequency of the action potentials may be detected in response to treatment of a cell with the agent. For example, an agent may shorten or lengthen the duration of action potentials or increase or decrease the frequency of action potentials.

In another aspect, a method of distinguishing different types of cells in a culture with a nanopillar electrode described herein may comprise: (a) measuring action potentials from one or more cells of the culture; and
(b) determining the cell type of one or more cells based on the shape, duration, or frequency of the action potentials. This method can be used to distinguish different types of excitable cells including, but not limited to neurons, muscle cells, and endocrine cells. In one embodiment, the method may comprise distinguishing different types of cardiac muscle cells, such as pacemaker cells and non-pacemaker cells.

In another aspect, a method of monitoring differentiation of a stem cell with a nanopillar electrode device described herein may comprise: (a) measuring action potentials from the stem cell during differentiation of the stem cell; and (b) detecting differentiation of the stem cell based on the action potentials having characteristics (e.g., shape, duration, and/or frequency) of a particular differentiated cell type. This method may be used to monitor differentiation of a stem cell into various types of excitable cells such as, but not limited to neurons, muscle cells (e.g., a cardiac muscle cell), or endocrine cells.

In any of the methods described herein, action potentials may be recorded from a single cell or a plurality of cells periodically over multiple consecutive days, for example, 2, 3, 4, 5 or more days.

In certain aspects, a method of fabricating a nanopillar electrode device described herein may comprise:
a) patterning a substrate with a plurality of metal leads and pads by photolithography;
b) passivating the surface of the substrate with a layer of $Si_3N_4/SiO_2$;
c) milling an array of holes through the layer of $Si_3N_4/SiO_2$ such that the metal pads underneath are exposed;
d) assembling nanopillar electrodes in the holes; and
e) electrically connecting the nanopillar electrodes with the metal pads.

In certain aspects, the passivation may be performed by plasma-enhanced chemical vapor deposition. In certain aspects, the milling may be performed by a focused gallium ion beam. In certain aspects, embodiment, the nanopillars are assembled by focused ion beam deposition. In certain aspects, the nanopillar electrodes may be assembled by electrodeposition.

In certain aspects, a method of fabricating a nanopillar electrode device described herein may comprise:
a) patterning a substrate with a plurality of metal leads and pads by photolithography;
b) passivating the surface of the substrate with a layer of $Si_3N_4/SiO_2$;
c) adding a layer of spin-coated e-beam photoresister to the surface of the substrate;
d) patterning a plurality of holes in the layer of spin-coated e-beam photoresister by using e-beam lithography;
e) exposing the metal pads underneath the holes by etching through the insulating layer of $Si_3N_4/SiO_2$;
f) growing nanopillar electrodes in the holes by electrodeposition; and
g) removing the e-beam photoresister.

These and other embodiments will readily occur to those of skill in the art in view of the disclosure herein.

BRIEF DESCRIPTION OF THE FIGURES

The skilled artisan will understand that the drawings, described below, are for illustration purposes only. The drawings are not intended to limit the scope of the present teachings in any way. Some of the drawings are not in scale.

FIG. 1a shows an optical image of a nanopillar electrode device with a four-by-four array of platinum pads and leads 100 connected to recording amplifiers. FIG. 1b shows a scanning electron microscopy (SEM) image of an array of five vertical nanopillar electrodes 140 on one of the platinum pads 110: the nanopillar electrodes 130 are 1.5 µm tall and have a diameter of 150 nm. The footprint of the nanopillar electrode array on each pad is 5×5 µm² or less. The pads 110 and leads are electrically insulated by a 350 nm $Si_3N_4/SiO_2$ layer 120. Most of the surface of the nanopillars is exposed for electrical detection. The inset to FIG. 1b is a schematic of a nanopillar electrode. FIG. 1c shows an optical image of HL-1 cells cultured on a glass coverslip with four arrays of electrodes (each array contains five nanopillars). There are no underlying platinum pads in this sample. The morphology of cells grown on vertical nanopillar electrodes is similar to the morphology of cells grown on planar substrates. FIG. 1d shows a SEM image showing four five-electrode arrays covered by an HL-1 cell. Arrows indicate the locations of nanopillar electrodes. FIG. 1e shows the cell-nanopillar electrode interface exposed by FIB milling shows that the nanopillar electrode is fully engulfed by the cell. FIG. 1f is a SEM image showing cellular protrusions reaching out to the nanopillar electrodes. All SEM images are taken at 52° to normal.

FIG. 2a shows that before electroporation, the recorded train of action potentials showed extracellular signatures. FIG. 2b shows that after electroporation, the recorded signal amplitude increased by a factor of greater than 100 and the shape exhibited intracellular features. Note that the y-axes in a and b have different scales. FIG. 2c shows a schematic (not to scale) of the electroporation of the cell membrane by a nanopillar electrode. Voltage pulses created nanoscale pores in the region of the cell membrane that surrounded the nanopillar electrode. FIGS. 2d and 2e shows evidence confirming that nanopillar electroporation had taken place. Confluent HL-1 cells were cultured on a three-by-three array of platinum pads in which the six pads in the second and third rows contained arrays of nine nanopillar electrodes, but the three pads in the top row contained milled holes but no nanopillars. We then introduced calcein, a membrane-impermeable dye, and performed electroporation. Comparison of the bright-field (FIG. 2d) and fluorescence (FIG. 2e) images of the same area confirmed that the calcein dye only entered those cells that contacted the nanopillar electrodes. No electroporation was observed on the top three control pads. Moreover, each array of nine nanopillar electrodes interfaced with just one cell. The cell on the top right (white arrow) is not directly over the electrode, but its membrane protrusion extends to the nearest nanopillar electrode site (FIG. 7).

FIG. 3a shows that after electroporation, the recorded action potential amplitude decays over time due to sealing of transient pores in the cell membrane. At 120 seconds after electroporation, the amplitude decays to 30% of its maximum value, but the action potential duration at 50% of the maximum (APD50) remains constant during this period (FIG. 8). About 10 minutes after electroporation, the recorded signal approaches an extracellular amplitude and shape. Three different segments of the recording are enlarged for clarity. The sealing of the cell membrane indicates that the intracellular recording is only invasive over a very short period of time compared to the lifetime of the cell in the culture. FIGS. 3b and 3c show intracellular recordings of action potentials of two types of HL-1 cells that are designated as pacemaker (FIG. 3b) and non-pacemaker (FIG. 3c) based on their shapes. Although the recorded amplitude decays, all five phases of the non-pacemaker action potential can still be readily observed 400 seconds after electroporation. In contrast, the pacemaker action potentials exhibit three phases with symmetric rising and falling edges.

FIG. 4a shows simultaneous intracellular recording with five different electrodes on the same culture. Electrodes A1, A2 and A3 are within 40 µm of one another, and electrodes B and C are separated by about 400 µm from one another and from electrodes A1-A3. Cardiomyocytes on electrodes A1-A3 undergo synchronized beating, but there are time delays with cardiomyocytes on electrodes B and C. The dotted line representing the same time is drawn to guide the eye. FIG. 4b shows extracellular (left) and intracellular (right) recording of a mature HL-1 cell over consecutive days. The shape and amplitude of the action potential exhibit minimal changes. Note that the y-axes on the left and right have different scales. FIG. 4c shows intracellular recording of an HL-1 cell in a developing culture over four consecutive days. We observed a transition from arrhythmic to rhythmic beating, a decrease in the beating interval, a significant change in the action potential shape and an increase in the maximum amplitude of the recorded action potential. (Note that the y-axes on the four traces have different scales.) FIG. 4d shows a histogram showing how the beating interval decreases from day 1 to day 4. (The 23 action potentials recorded immediately after each electroporation were analyzed; error bars represent one standard deviation.).

FIG. 5a shows extracellular action potentials recorded by nanopillar electrodes (bottom), and intracellular action potentials recorded by nanopillar electrodes after electroporation (top) after nifedipine (a $Ca^{2+}$ channel blocker) is administered to HL-1 cells (red lines). Changes in the duration and period of the action potential with respect to a control experiment (blue line) are much clearer in the intracellular recordings. FIG. 5b shows that similar results were found when tetraethylammonium (a $K^+$ channel blocker) was administered. The rising edges of the first action potential in each pair of traces were overlaid to allow comparison (note that the vertical scale bars are different). FIG. 5c shows that nifedipine leads to a reduction in the APD50 relative to the control, and tetraethylammonium (TEA) leads to an increase. For each drug, four different HL-1 cells on three different cultures were measured (see Tables 1 and 2 for further details).

FIG. 6a shows a picture of the assembled nanopillar electrode device. The plastic well at the center surrounds the nanopillar electrodes and hosts the HL-1 cell culture. The quartz chip in the center is glued to a custom-designed printed circuit board and Pt leads are electrically connected via wire bonding. FIG. 6b shows a SEM image of custom-made 4×4 multielectrode arrays coated with a 350 nm $Si_3O_4/SiO_2$ insulation layer. FIG. 6c shows that on this Pt pad, three nanopillar electrodes are constructed by first FIB milling of holes through the passivation layer and then FIB-assisted Pt deposition. FIG. 6d shows the dimension of fabricated nanopillar electrodes. The nanopillar electrodes are electrically connected to the bottom Pt pad.

FIG. 9a shows the duration of action potentials at 50% of amplitude (APD50) and action potential period recorded by the nanopillar electrodes after electroporation of HL-1 cells administered with nifedipine at 100 nM and 300 nM concentrations. FIG. 9b shows the recorded APD50 and action potential period with tetraethylammonium at 1 mM and 10 mM. Error bars are standard deviations of 30 action potentials.

FIG. 11a is a schematic of cells interfacing with planar, solid nanopillar 1110, and hollow nanopillar (nanotube 1120) electrodes. FIG. 11b is an SEM image of a three-by-three array of iridium oxide (IrOx) nanotube electrodes showing hollow cores. The inset of FIG. 11b shows the top view of an IrOx nanotube electrode. FIG. 11c is an SEM image of a three-by-three array of gold (Au) nanopillar electrodes showing solid cores. FIG. 11d provides an augur electron spectrum of the nanotube electrodes which confirm the presence of iridium an oxygen. The insets of FIG. 11d show the raw spectra of oxygen an iridium. FIG. 11e provides an elemental line scan along the diameter of an IrOx nanotube and a Au solid nanopillar. FIG. 11f provides the electrochemical impedance spectroscopy of IrOx nanotube and Au solid nanopillar electrodes of the same surface area in PBS. FIG. 11g provides the cyclic voltammetry of IrOx nanotube and Au solid nanopillar electrodes of the same surface area in PBS observed at a scan rate of 30 mV/s.

FIG. 12a shows fluorescent images of live HL-1 cardiomyocytes after growing for 3 and 7 days on Au film, IrOx film, Au solid nanopillar arrays and IrOx nanotube arrays. Cells were stained with calcein AM and propidium iodide on day 3 and 7. The white arrows mark cells that uptook propidium iodide. FIG. 12b shows a comparison of viability of HL-1 cells grown on Au film, IrOx film, Au solid nanopillar arrays and IrOx nanotube arrays. FIG. 12c is a set of SEM images of a cardiomyocyte growing on top of vertical IrOx nanotube arrays show the cell engulfs the nanotubes. The apical membrane protrudes into the nanotubes, showing both positive and negative membrane curvature. FIG. 12d is a set of SEM images of an unroofed cell with part of the apical plasma membrane and the nucleus removed. Expanded images show the basal membrane wraps around the nanotube and extends into the nanotube.

FIG. 13a is a schematic of the experiment. FIG. 13b shows an intracellular recording of HL-1 action potentials by IrOx nanotube and Au solid nanopillar electrodes for the first 60 s after electroporation. FIG. 13c shows a time evolution of recorded action potentials amplitude by IrOx nanotube and Au nanopillar electrodes. Arrows indicate recorded amplitude step drops. The insets are expanded views of drop 1 and 4. FIGS. 13d and 13e provide a comparison of intracellular recorded signal amplitude (d) and decay time (e) between IrOx nanotube and Au solid nanopillar electrodes. FIG. 13f shows a simultaneous recording at six different electrodes in the same culture. Adjacent electrode separation is 100 μm and the electrode positions on the chip are shaded. The vertical dashed lines represent the same time to guide eyes. FIG. 13g shows a recording of a single cell over eight consecutive days.

FIG. 14a-c shows recorded action potential decays in a combination of linear decays (a), exponential decays (b), and step drops (b and c). The inset of FIG. 14c shows the change in recorded signal at the last drop. FIG. 14d shows the distribution of drop durations. FIG. 14e shows an inverted microscope view of a cardiomyocyte (dashed-line circle) being simultaneously recorded. FIG. 14f-h provide a Simultaneous recording of membrane potential by IrOx nanotube electrodes and whole-cell current clamp before electroporation (f) and after electroporation (g, h).

FIG. 15a shows the patterning of a Pt pad and line by photolithography and subsequent electrical insulation by Si3N4/SiO2 deposition (top), and an overhead view of 8×8 arrays of Pt pads and lines (bottom). FIG. 15b shows nanohole patterning on resist by electron beam lithography and subsequent clearing of the underneath $Si_3N_4/SiO_2$ by plasma etching (top), and a side view of this process (bottom). FIG. 15c shows electrodeposition of a 3×3 array of IrOx nanotubes on each Pt pad and subsequent removal of resist.

DEFINITIONS

Figure 1:
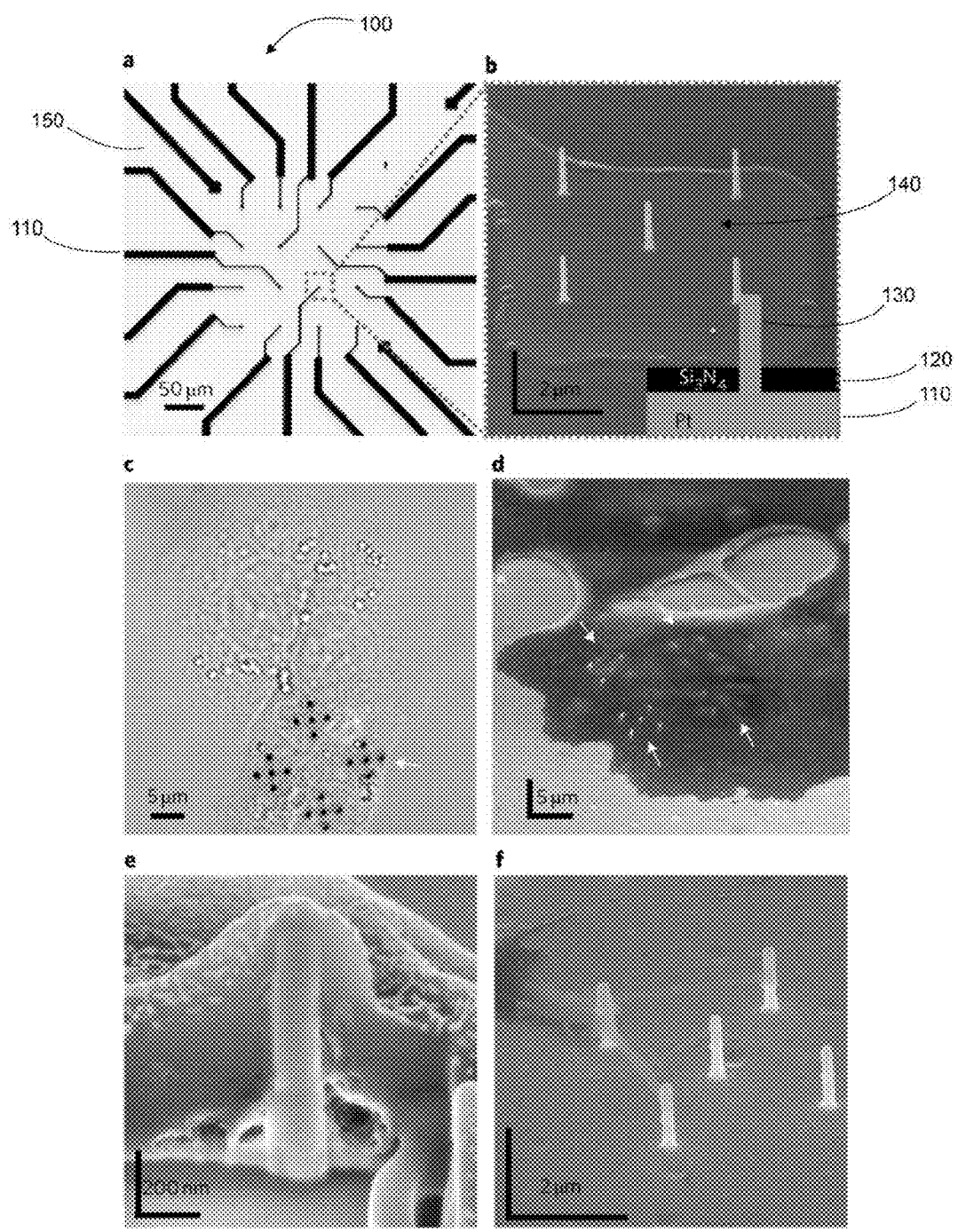
FIG. 1 shows nanopillar electrode devices and their interactions with HL-1 cardiomyocytes.

Before describing exemplary embodiments in greater detail, the following definitions are set forth to illustrate and define the meaning and scope of the terms used in the description.

As used herein, the phrase "attached to" refers to a physical connection between one component of a system and another, which can be direct or indirect.

The term "electrical connection" refers to a connection or path that allows for the directional flow of an electric charge. In certain aspects, an electrical connection may be controlled by a switch or a gate.

The terms "impedance" and "electrical impedance" are used interchangeably and refer to the complex ratio of voltage to current in an electric circuit, component or structure.

The term "nanostructure" as used herein refers to a structure of nano-scale dimensions along at least one axis. Nano-scale dimensions may be less than 1 μm, e.g., 1 nm to 5 nm, 5 nm to 10 nm, 10 nm to 20 nm, 20 nm to 50 nm, 50 nm to 100 nm, 100 nm to 200 nm, 200 nm to 500 nm, or any combination thereof.

The term "aspect ratio" as used herein refers to the ratio of the length of a first axis of a nanostructure to the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

The term "nanopillar" refers to a nanostructure that has one principle axis that is longer than the other two principle axes. Consequently, a nanopillar has an aspect ratio greater than one. The term "nanopillar" as used herein encompasses nanostructures that are solid or hollow, including nanostructures commonly referred to as nanorods, nanotubes and nanowires. The nanopillars described herein can be substantially homogeneous in material properties, or in certain embodiments can be heterogeneous. The nanopillars can be fabricated from essentially any convenient material or materials by any convenient method known in the art. The nanopillars can comprise "pure" materials, substantially, pure materials, doped materials and the like, and can include insulators, conductors, and semiconductors. The "diameter" or "width" of a nanopillar refers to the diameter of a cross-section normal to the major principle axis (the long axis) of the nanopillar. Where the cross-section is not circular, the diameter is the average of the major and minor axes of that cross-section. Nanopillars can have a variable diameter or can have a substantially uniform diameter, that is, a diameter that shows a variance less than about 20% (e.g., less than about 10%, less than about 5%, or less than about 1%) over the region of greatest variability and over a linear dimension of at least 5 nm (e.g., at least 10 nm, at least 20 nm, or at least 50 nm).

The term "electrode" as used herein refers to a structure having an electrical conductivity higher than the electrical conductivity of material to which it is exposed. As used herein, an electrode in "electrical proximity" to a cell refers to a distance which is sufficiently close to transmit electrical stimuli to the cell or receive electrical signals from the cell.

The term "nanopillar electrode device" as used herein refers to a device comprising one or more nanopillar electrodes. In certain aspects, a nanopillar electrode device is capable of measuring cellular electrical signals (e.g., intracellular or extracellular).

As used herein, an "array" of articles (e.g., an array of nanopillar electrodes) comprises one or more of said articles. When the array comprises a plurality of articles, the articles may be arranged in one, two, or three dimensions and may or may not be aligned with one another.

The term "plurality," as used herein, means two or more.

The terms "metal pad" and "pad" can be used interchangeably and refer to an area on an apparatus or a device which is electrically connected to at least one electrode on the device and which can be operatively connected to an electrical circuit (e.g., an impedance measurement circuit or a signal source or an recording amplifier). The electrical connection between a connection pad and an electrical circuit can be direct or indirect, through any appropriate electrical conduction means such as leads or wires. Such electrical conduction means may also go through electrode or electrical conduction paths located on other regions of the apparatus or device.

The term "reference electrode" refers to an electrode that has a stable potential, against which the potential of another electrode can be measured. In the context of measuring action potentials in cells, the reference electrode may be exposed to the extracellular environment and not the membrane of a cell.

The term "amplifier", "recording amplifier" and "voltage amplifier" are used interchangeably and refer to a component of the circuit that produces an output potential that is greater than an input potential. An amplifier may have a plurality of channels, and may be capable of amplifying a plurality of inputs.

The term "electrical lead" and "metal lead" are used interchangeably and generally refer to a conductive wire that electrically connects two points.

The term "footprint" as used herein refers to the surface area of a device or a component of a device such as a metal pad, electrode, array of electrodes, and so forth.

The term "substrate," refers to any solid object on which a mounted material may be optionally immobilized. Essentially any conceivable substrate may be used within the methods provided herein, including biological, nonbiological, organic and inorganic substrates, as well as substrates that are a combination of any of these. The substrate may have any convenient shape. The substrate may form a rigid support on which to support a mounted material, and is preferably flat, although it may take on a variety of alternative surface configurations, including having raised and/or depressed regions.

As used herein, the term "chamber" refers to any container on or in which cells may be cultured. The chamber may be sealable from an external environment. The chamber may be clear or semi-transparent.

The term "printed circuit board" refers to a semiconductor chip including electronic elements fabricated into the chip or onto the surface of the chip (e.g., silicon, GaAs, SiGe, SiC).

As used herein, the term "patterning" refers to creating a layout of features (e.g., nano or micro-scale structures). In certain aspects, patterning may involve the creation of features having recurring relationships to one another (such as size, shape, and relative position). Patterning may be performed multiple times to create similar layouts of features. Patterning may be achieved through lithography, etching, milling, deposition, and other fabrication techniques.

As used herein, "passivation" refers to the deposition of a layer (a "passivation layer") of protective material. The protective material may electrically insulate an underlying material and/or act as a diffusion barrier against water, solubilized ions, corrosive or otherwise damaging materials, and so forth.

As used herein, the terms "light" and "electromagnetic radiation" can be used interchangeably and can refer to light or electromagnetic radiation in the ultraviolet, visible, near infrared and infrared spectra. The terms can further more broadly include electromagnetic radiation such as radio waves, microwaves, x-rays, and gamma rays. Thus, the term "light" is not limited to electromagnetic radiation in the visible spectrum.

The term "photoresist" refers to a material that, upon irradiation with light, sustains a chemical reaction that allows irradiated and non-irradiated regions to be separated from one another. Although the separation may be simultaneous with irradiation (e.g., in laser ablation), it may require an additional process step or steps (e.g., exposure to a developer). The chemical reaction may involve the formation or breakage of chemical bonds with such bond changes occurring in either an intramolecular or intermolecular fashion. In some applications, a photoresist is applied to a flat surface as a relatively thin liquid layer and evaporated.

The term "e-beam resist", "e-beam resistor" and "e-beam photoresistor" can be used interchangeably and refer to an electron sensitive film of which electron beam exposed or unexposed regions may be removed. Although the separation may be simultaneous with e-beam radiation, it may require an additional process step or steps (e.g., exposure to a developer)

The term "focused ion beam resist" or "ion beam resist" refers to an ion beam sensitive film of which electron beam exposed or unexposed regions may be removed.

The term "resist" and "resist film" are used interchangeably and may refer to a photoresist, an e-beam resist or an ion beam resist.

The term "spin-coating" refers to the process of depositing a coating material on a flat surface and spinning said surface so as to uniformly spread the coating material across said surface. In certain aspects, the flat surface may be a substrate and the coating material may be a resist such as a photoresist or e-beam resist.

The term "lithography" refers to the use of irradiation to imprint a design on a surface. "Lithography" encompasses a number of techniques, including photolithography, electron-beam lithography, and focused ion beam lithography. In some cases, portions of the surface which are exposed to the irradiation (e.g., light, e-beam, ion beam, etc.) are either retained or lifted off, simultaneously with irradiation or after exposure to, for example, a chemical agent.

The term "milling" as used herein refer to the removal of material during device fabrication by irradiation, such as light irradiation, an electron-beam, a focused ion beam, and so forth.

The term "etching" refers to the removal of material during device fabrication. Methods of etching include chemical etching, wet etching and plasma etching.

The term "assembling" and "growing" are used interchangeably herein and refer to the deposition of material to form a structure, such as a nanostructure.

The term "deposition" in the context of the formation of a thin layer (i.e., of nano or micro-scale thickness) of material during device fabrication refers to any of a number of techniques suitable for formation of a thin layer, including both chemical deposition and physical deposition techniques. Chemical deposition techniques include spin coating, electroplating, chemical solution deposition, chemical vapor deposition (such as plasma-enhanced chemical vapor deposition), and atomic layer deposition. Physical deposition techniques include thermal deposition, laser deposition, electrospray deposition, and ion beam deposition (such as focused gallium ion beam deposition).

The term "electrodeposition", "electroplating" and "electrochemical deposition" are used interchangeably to refer to the deposition of material (e.g., from solution or an ionized gas) by the application of an electric voltage. In certain aspects, electrodeposition involves at least one of depositing a film and assembling a structure on a substrate.

As used herein, "biocompatible metal" refers to a metal or oxide thereof that does not have deleterious effects on cells, including the viability, attachment, spreading, motility, growth, cell division or cell beating.

The term "electroporation" as used herein refers to the process of permeabilizing a cell membrane (making it permeable to particles such as small molecules, ions, electrons, and the like) through the application of an electric current. Electroporation may result in local or systemic permeabilization of a cell membrane, based on voltage, duration, repetition, location and proximity of application.

The term biphasic as used herein refers to an electric pulse with two parts, each with an opposite polarity. The two parts need not be of similar magnitude or duration.

The term "membrane potential" refers to the electrical potential difference across a cell membrane created by ion transport through channels and pumps in the cell membrane. Some of these channels are passive, so that ions may move through the channel diffusively or by electrical gradient forces acting on them. The electrochemical equilibrium condition that exists is a balance of the diffusion and electrical forces. Others are chemically gated, voltage gated, or have active pumps that move ions across the membrane. Changes in membrane potential can be stimulated by various means, e.g. electrical charge, addition of channel modulating compounds, etc.

The term "action potential" refers to a sudden change in the electrical state of the membrane of a cell. For example, the membrane potential may change from about −70 mV to +40 mV during a neuronal cell action potential. A specific series of ion channel events are associated with an action potential. For example, in a neuronal cell voltage gated $Na^+$ channels open when the membrane potential rises about 20 mV above the resting potential; this potential is called the "threshold".

The term "test compound" or "agent" refers to any biological compound whose activity or direct or indirect effect or effects on cells is investigated in any assay. An agent can be any compound, including, but not limited to, a small molecule, a large molecule, a molecular complex, an organic molecule, an inorganic molecule, a biomolecule or biological molecule such as but not limited to a lipid, a steroid, a carbohydrate, a fatty acid, an amino acid, a peptide, a protein, a nucleic acid, or any combination thereof. An agent can be a synthetic compound, a naturally occurring compound, a derivative of a naturally-occurring compound, and so forth. The structure of a test compound can be known or unknown.

DETAILED DESCRIPTION

This disclosure provide a nanopillar electrode device. With reference to FIG. 1, a nanopillar electrode device may comprise a substrate 150 patterned with a plurality of metal pads 100; a plurality of nanopillars electrode arrays 140, wherein each nanopillar electrode array 140 is attached to the substrate 150 above a metal pad 110 and electrically connected to the pad 110; and a chamber 160 surrounding the nanopillar electrodes 130, which can be used for culturing cells of interest for recording action potentials. The device may further comprise one or more recording amplifiers, wherein each recording amplifier is electrically connected to a metal pad by an electrical lead. See FIG. 1a-1f, FIG. 6a-6d, and FIG. 10 for a depiction of exemplary nanopillar electrode devices.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise, e.g., when the word "single" is used. For example, reference to "a nanopillar" includes a single nanopillar and multiple nanopillars. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications mentioned herein are incorporated herein by reference to disclose and describe the methods and/or materials in connection with which the publications are cited.

The practice of the present invention may employ, unless otherwise indicated, conventional methods of neurobiology, medicine, cell biology, nanotechnology, biochemistry, and recombinant DNA techniques, within the skill of the art. Such techniques are explained fully in the literature. See, e.g., B. Sakmann and E. Neher Single-Channel Recording, $2^{nd}$ edn (Springer, 2009); R. D. Purves, *Microelectrode Methods for Intracellular Recording* (Academic Press, 1981); F. Rahman, *Nanostructures In Electronics And Photonics* (Pan Stanford Publishing, 2008); A. L. Lehninger, *Biochemistry* (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.) which are incorporated herein by reference.

In further describing embodiments of the invention, embodiments of the device will be described first in greater detail. Next, embodiments of methods of use and methods of fabrication are described.

Devices

A nanopillar electrode device may have a substrate patterned with one or more metal pads. Any convenient substrate may be used within the methods provided herein, including biological, nonbiological, organic and inorganic substrates, as well as substrates that are a combination of any of these. The substrate may comprise functionalized glass, Si, Ge, GaAs, GaP, $SiO_2$, $SiN_4$, modified silicon, photoresist, biolayers, saline layers or any one of a wide variety of polymers such as polytetrafluoroethylene, polyvinylidenedifluoride, polystyrene, polycarbonate, polyethylene, polypropylene, nylon or combinations thereof. Substrates also include silicon on insulator structures, epitaxial formations, germanium, germanium silicon, polysilicon, amorphous silicon, glass, quartz, or gel matrices and/or like substrates, non-conductive, semi-conductive or conductive. In certain embodiments, the substrate may be of any suitable transparent material, such as quarts or glass (e.g., fused silica). In addition, the substrate may have any convenient shape, such as a disc, square, sphere, circle, or any other suitable shape, and may be formed, for example, as a wafer, particle, strand, precipitate, gel, sheet, tubing, sphere, container, capillary, pad, slice, film, plate or slide. The substrate may be purchased from any of a number of sources. The substrate may be sectioned to any suitable size, such as 10 $\mu m^2$ to 100 $\mu m^2$, 100 $\mu m^2$ to 1000 $\mu m^2$, 1000 $\mu m^2$ to 10000 $\mu m^2$, 10000 $\mu m^2$ to 0.1 $mm^2$, 0.1 $mm^2$ to 1 $mm^2$, 1 $mm^2$ to 10 $mm^2$, 10 $mm^2$ to 100 $mm^2$, 100 $mm^2$ to 1000 $mm^2$, 10000 $mm^2$ to 0.1 $cm^2$, 0.1 $cm^2$ to 1 $cm^2$, 1 $cm^2$ to 10 $cm^2$, and so forth.

A metal pad (i.e., one or more metal pads of the nanopillar electrode device) may be of any suitable conductive material. In addition, the metal pads may be of a biocompatible material, such as platinum, titanium, silver, gold, titanium, iridium or an oxide thereof. The footprint of the metal pad may be any suitable size. In some cases, the footprint of the metal pad may be at or between 1 $\mu m^2$ and 1 $cm^2$, e.g., 0.1 $\mu m^2$ to 1 $\mu m^2$, 1 $\mu m^2$ to 10 $\mu m^2$, 10 $\mu m^2$ to 100 $\mu m^2$, 100 $\mu m^2$ to 1000 $\mu m^2$, and so forth. In certain aspects, the footprint of a metal pad may be such that it would likely overlap with only one cell. For example, the footprint of a metal pad may be less than or equal to 5×5 $\mu m^2$.

The surface of the substrate and metal pads may be passivated with any suitable protective material. The material may protect the underlying substrate and/or metal pads from corrosion or other damage from an external environment, may act as a diffusion barrier against small molecules and/or solubilized ions, may act as an electrical insulator, or any combination thereof. In certain aspects, the protective material may be a pasivating oxide, such as a silicon nitride, silicon dioxide, titanium dioxide, aluminum oxide, any other suitable protective oxide, or a combination thereof. In certain aspects, the protective material may form a layer that is between 50 nm and 1 μm thick, e.g., 50 nm to 100 nm, 100 nm to 200 nm, 200 nm to 300 nm, 300 nm to 400 nm, 400 nm to 500 nm, 500 nm to 600 nm, 600 nm to 700 nm, 700 nm to 800 nm, 800 nm to 900 nm, or 900 nm to 1 μm thick. In one example, the surface of the substrate and metal pads may be passivated with a layer of $Si_3N_4/SiO_2$ about 350 nm thick.

The metal pad may comprise an array of one or more nanopillar electrodes. The array may comprise anywhere from one nanopillar electrode to one million, depending on the application. In certain aspects, the array may comprise 1-10 nanopillar electrodes, 10-20 nanopillar electrodes, 20-50 nanopillar electrodes, 50-100 nanopillar electrodes, 100-500 nanopillar electrodes, 500-1000 nanopillar electrodes, and so forth. In one example, the array may be a 3×3 array of nanopillar electrodes. In another example, the array may be a 4×4 array of nanopillar electrodes. Nanopillar electrodes in an array may or may not be of uniform size (e.g., length, diameter), structure, and/or distribution. As will be further discussed in the Experimental section, an increase in the number of nanopillar electrodes in an array may reduce impedance and improve signal strength.

A nanopillar electrode (i.e., one or more nanopillar electrodes arrayed on the metal pad) may be of any suitable conductive material. In certain aspects, the nanopillar electrode is of a biocompatible material, such as platinum, titanium, silver, gold, titanium, iridium or an oxide thereof. The nanopillar electrode may be of any suitable structure having an aspect ratio of more than 1. The nanopillar electrode may have an aspect ratio greater than 1, greater than 2, greater than 5, greater than 10, greater than 20, greater than 50, or greater than 100, and so forth. The nanopillar electrode is substantially straight and having an even surface or may be irregular in surface, overall shape and/or length. The nanopillar electrode may be solid or hollow along all or part of the length of the nanopillar. In one example, the nanopillar electrode may be a solid platinum nanopillar. In another example, the nanopillar electrode may be a iridium oxide nanotube. The width (or diameter) of the nanopillar may be a nano-scale dimension, such as between 1 nm and 1 μm. In certain aspects, the width of the nanopillar may be 1 nm to 5 nm, 5 nm to 10 nm, 10 nm to 20 nm, 20 nm to 50 nm, 50 nm to 100 nm, 100 nm to 200 nm, 200 nm to 300 nm, 300 nm to 400 nm, 400 nm to 500 nm, 500 nm to 600 nm, 600 nm to 700 nm, 700 nm to 800 nm, 800 nm to 900 nm, or 900 nm to 1 μm. In certain aspects, the width of the nanopillar electrode may be variable along its length. The length (along the longest axis) of the nanopillar electrode may be on the nano or micro-scale. In certain aspects, the length of the nanopillar may be 10 nm, 20 nm, 50 nm, 100 nm, 200 nm, 500 nm, 1 μm, 2 μm, 5 μm, 10 μm, 50 μm, and so forth.

In certain aspects, the nanopillar electrode may be hollow. The wall thickness of a hollow nanopillar electrode may be anywhere from 1 nm to 200 nm. For example, the wall thickness of a hollow nanopillar electrode may be 1 nm to 2 nm, 2 nm to 5 nm, 5 nm to 10 nm, 10 nm to 20 nm, 20 nm to 30 nm, 30 nm to 40 nm, 40 nm to 50 nm, 50 nm to 60 nm, 60 nm to 70 nm, 70 nm to 80 nm, 80 nm to 90 nm, 90 nm to 100 nm, 100 nm to 150 nm, 150 nm to 200 nm, and so forth. The base of a hollow nanopillar electrode (e.g., the end in contact with the metal pad) may be open or closed.

A nanopillar electrode on a metal pad may protrude through the passivation layer and thereby be exposed to the external environment. The nanopillar electrode may be capable of spontaneously forming a close association with a cell membrane. In certain aspects, the nanopillar electrode may be hollow and a cell membrane may spontaneously form positive and negative curvature along the surface of the nanopillar electrode and may protrude into the hollow cavity of the nanopillar electrode.

In certain aspects, a chamber may surround the nanopillar electrodes. The substrate, metal pads, and nanopillar electrode array may be placed in the chamber, adhered to the chamber, or embedded in the chamber. The chamber may be of any material and design so as to allow the adherence of cells. The chamber may or may not be of a transparent material, such as glass or plastic, depending on the potential applications, such as microscopy. The chamber may be sealable, or may be partially open to the environment. In one example, the chamber may be a slide and/or coverslip, with the substrate, metal pads, and nanopillar electrode array on one side (e.g., the coverslip or slide). In another example, the chamber may contain enough volume so as to provide media to a cell culture for one or more days. The surface of the substrate may be coated with a cell-adhesive agent such as fibronectin, collagen, laminin, and so forth.

In other aspects, the nanopillar electrode device may not comprise a chamber and may be suitable for direct implant into the nervous system of any suitable animal, such as mammal (human, mouse, rat, and so forth).

The metal pad may be attached to a metal lead (e.g., during the original patterning of metal pads). The metal pad may be electrically connected, directly or indirectly, to a recording amplifier through the metal lead. In certain aspects, the recording amplifier may comprise a plurality of channels electrically connected to a plurality of metal pads through a plurality of metal leads. The number of channels may be anywhere from 1 to 10000, e.g., 1 to 5, 5 to 10, 10 to 20, 20 to 50, 50 to 100, 100 to 200, 200 to 1000, 1000 to 5000, 5000 to 10000, and so forth.

In certain aspects, the nanopillar electrode device may further comprise an integrated circuit (i.e., a circuit board) that interfaces with leads from one or more metal pad and/or with leads from one or more recording amplifiers. The circuit board may be electrically connected by wire bonding according to any convenient technique such as ball bonding and compliant bonding.

Methods of Device Fabrication

A nanopillar electrode device according to the embodiments described herein may be fabricated by any of a number of suitable methods.

A substrate, as described previously, may be patterned with one or more metal pads and leads. The metal pads and leads may be patterned by lithography, such as photolithography, electron beam lithography or focused ion beam lithography. In certain aspects, lithography may enable or prevent the deposition or liftoff of a conductive metal onto regions of a resist that are exposed to the radiation (e.g., light, electron beam, focused ion beam, etc.). Standard lithography methods are provided in F. Rahman, *Nanostructures In Electronics And Photonics* (Pan Stanford Publishing, 2008), which is incorporated herein by reference. As discussed previously, the metal pads and leads may comprise any of a number of conductive metals, such as platinum, titanium, silver, gold, titanium, iridium or an oxide thereof.

In certain aspects, the surface of the substrate may be passivated with a thin layer of deposited material such as a silicon nitride, silicon dioxide, titanium dioxide, aluminum oxide, or any protective oxide known to one of ordinary skill in the art. The passivation layer may be deposited by any suitable number of methods, such as atomic layer deposition, chemical vapor deposition (e.g., plasma-enhanced chemical vapor deposition), chemical solution deposition, physical vapor deposition, electrospray deposition, electrodeposition, ion beam deposition and so forth.

In certain aspects, a resist may be deposited in a thin layer by any suitable method. One or more holes may be milled in the resist by any suitable method, including irradiation with any of a laser, electron-beam, focused ion beam, and so forth. For example, a thin layer of chromium (the resist) may be milled using a focused gallium ion beam to form a 250 nm diameter hole.

Lithography (e.g. photolithography, electron beam lithography) and/or etching (e.g. plasma etching) may be utilized to pattern a nanohole in the passivation layer, thereby exposing the underlying metal pad.

Nanopillar electrodes may be grown by any suitable technique, depending on the desired nanopillar structure and starting material. In certain aspects, nanopillar electrodes may be grown by chemical deposition (e.g., including spin coating, electroplating, chemical solution deposition, chemical vapor deposition such as plasma-enhanced chemical vapor deposition, atomic layer deposition, and so forth) or physical deposition (e.g., thermal deposition, laser deposition, electrospray deposition, ion beam deposition such as focused gallium ion beam deposition, and so forth). For example, platinum nanopillar electrodes may be grown by focused ion beam deposition as described further in Experiment 1. In another example, iron oxide hollow nanopillars (nanotubes) may be grown by electrodeposition, as described further in Experiment 2. Electrodeposition of iron oxide nanotubes is also discussed in *Synthesis of Iridium Oxide Nanotubes by Electrodeposition into Polycarbonate Template* (Mafakheri, E. et al. Electroanal 23, 2429-2437 (2011)) which is incorporated herein by reference.

In certain aspects, a resist may be removed after the electrode fabrication by any convenient method. For example, a resist may be removed to allow transparency for microscopy applications or to prevent damage to cells to be cultured on the nanopillar electrode device.

The metal pad may be attached to a metal lead (e.g., during the original patterning of metal pads). The metal pad may be electrically connected, directly or indirectly, to a recording amplifier through the metal lead. In certain aspects, the nanopillar electrode device may further comprise an integrated circuit (i.e., a circuit board) that interfaces with leads from one or more metal pad and/or with leads from one or more recording amplifiers. The circuit board may be electrically connected by wire bonding according to any convenient technique such as ball bonding and compliant bonding.

The recording amplifier, may be configured to amplify the voltage input from the metal pad by anywhere from 10 fold to ten thousand times. In certain aspects, the recording amplifier may be configured to amplify the voltage input by around 10×, 100×, 1000×, or 10000×. Amplification may be reduced for intracellular measurements of action potential as oppose to extracellular measurements. For example, the amplification for an intracellular measurement of action potential may be 110×, while the amplification for an extracellular measurement of action potential may be 1110×. In certain aspects, the recording amplifier may be electrically connected to a plurality of metal pads through a plurality of metal leads.

Measurements may be taken at any convenient sampling rate, such as a sampling rate of less than 10 Hz, 10 Hz to 50 Hz, 50 Hz to 100 Hz, 100 Hz to 200 Hz, 200 Hz to 500 Hz, 500 Hz to 1 kHz, 1 kHz to 5 kHz, 5 kHz to 10 kHz, 10 kHz to 20 kHz, 20 kHz to 50 kHz, 50 kHz to 100 kHz, 100 kHz to 200 kHz, 200 kHz to 500 kHz, 500 kHz to 1 MHz, although rates outside of these ranges may be used in certain circumstances. The signal may be filtered with any suitable band pass of, for example, 1 Hz to 5 kHz.

Methods of Use

The nanopillar electrode devices of the embodiments discussed herein find use in a variety of applications including cell electrophysiology measurements with single cell resolution. The device may be used to measure action potentials in a number of cell types, including neurons, muscle cells (such as a cardiac muscle cell), endocrine cells, and cell subsets thereof. A plurality of nanopillar electrodes of an array on a metal pad may be placed in contact with a single cell, with each nanopillar electrode in contact with different portions of the cell membrane. In certain aspects, a cell may be pinned down by a nanopillar electrode array (for example, to prevent cell migration). In certain aspects, action potentials of a plurality of cells may be simultaneously measured through a plurality of metal pads.

The nanopillar electrode device may be used to take extracellular or intracellular measurements of action potentials. A cell may be electroporated to allow for intracellular measurements of action potential. In certain aspects, electroporation may be performed by a voltage pulse through one or more nanopillar electrodes. The electroporation may be local (restricted to a region of the cell membrane surrounding one or more nanopillar electrodes). Due to the close association of the nanopillar electrode, the voltage pulse may not need to be of high voltage or long duration to achieve local electroporation. In certain aspects, the voltage pulse may be anywhere from 0.5 V to 50 V. For example, the voltage pulse may be at or between 1 to 5 V, 0.5 to 10 V, 0.5 to 50 V, more than 0.5 V, more than 2 V, less than 2 V, less than 5 V, less than 10 V, although voltages outside of these ranges may be used in certain circumstances The duration of the voltage pulse may be in the micro or millisecond range. For example, the duration of the voltage pulse may be at or between 1 μs to 10 μs, 10 μs to 20 μs, 20 μs to 50 μs, 50 μs to 100 μs, 100 μs to 200 μs, 200 μs to 500 μs, 500 μs to 1 ms, 1 μs to 2 ms, 2 μs to 5 ms, 5 μs to 10 ms, 10 μs to 20 ms, 20 μs to 50 ms, 50 μs to 100 ms, 100 μs to 200 ms, 200 μs to 500 ms, 500 μs to 1 s, 1 s to 2 s, 2 s to 5 s, 5 s to 10 s, although durations outside of these ranges may be used in certain circumstances. Higher voltage pulses and/or durations may improve signal strength or duration of intracellular measurements of action potential, but may be more invasive (may increase damage to the cell). Voltage pulses may be repeated any number of times over any period of time. For example, voltage pulses may be repeated anywhere from 1 to one thousand times over 10 ms, 50 ms, 100 ms, 200 ms, 500 ms, 1 s, 2 s, 5 s, 10 s, although rates outside of these ranges may be used in certain circumstances. In one example, biphasic pulses at 2.5 V for 200 microseconds may be performed, and may be repeated for 20 pulses over 1 second. In certain aspects, measurement of action potentials may be delayed after electroporation by anywhere from 1 s to 10 minutes. For example, measurement of action potentials may be delayed by 10 ms to 100 ms, 100 ms to 1 s, 1 s to 2 s, 2 s to 5 s, 5 s to 10 s, 10 s to 20 s, 20 s to 1 min, 1 min to 2 min, 2 min to 5 min, 5 min to 10 min, although delays outside of these ranges may be used in certain circumstances. In certain aspects, electroporation may be repeated upon full or partial membrane recovery, as would be observed by a decrease in the signal strength of the measured action potentials.

In certain aspects, the nanopillar electrode device may be used to measure differences in action potential over time or between cells. Differences in action potential may include differences in the shape, duration and/or frequency.

Measurement of differences in action potential may be used in an assay or screen of an agent may affect cell electrophysiology. In certain aspects, the agent may be an agent that is an ion channel blocker, a ligand for an ion channel performing an agonistic or antagonistic role, a hormone, a second messenger, and so forth. Ion channels that may be affected by the agent include potassium, calcium, sodium or proton channels involved in active or passive transport. The agent may shorten or lengthen the duration of action potentials, or may increase or decrease the frequency of action potentials.

Measurement of differences in action potential may be used to distinguish cells in a cell culture (e.g., based on shape, duration, and/or frequency of the action potentials). For example, measurement of differences in action potential may be used to distinguish pacemaker from non-pacemaker cells. In certain aspects, measurement of differences in action potential may be used to monitor differentiation of a stem cell into, for example, a neuron, a muscle cell (e.g. a cardiac muscle cell), an endocrine cell, or a subset thereof.

Measurement of cell action potentials may be combined with microscopy. In certain aspects, appropriate sample preparation and microscopy may be performed to reveal expression of cellular markers and cellular processes which may be correlated with the measurements of action potentials to provide a comprehensive profile of the electrophysiology of a cell.

The nanopillar electrode device of certain embodiments disclosed herein may be suitable in vivo, such as for making in vivo neural recordings in mammals (humans, rodents, etc.). A discussion of applications of nano-scale electrodes in in vivo neural recordings may be found in *Nanowire-based electrode for acute in vivo neural recordings in the brain* (Suyatin D. B. et al. (2013) PLoS One. 8(2):e56673), which is incorporated herein by reference.

Utility

Nanopillar electrode devices and methods of recording action potentials with such devices are disclosed. In particular, nanopillar electrode devices can be used to record both extracellular and intracellular action potentials of cells with excellent signal strength and quality. Nanopillar electroporation is used to increase the permeability of cell membranes to allow intracellular recording. Nanometer-sized pores, generated in a cell membrane by electroporation, may seal within a number of minutes. Thus, intracellular recording following electroporation with nanopillar electrodes is minimally invasive and allows repetitive recording on multiple cells, in parallel, over several consecutive days. Moreover, because cells quickly reseal after electroporation, it is possible to repeatedly switch between extracellular and intracellular recording. The close association between the cell membrane and a nanopillar electrode of a number of the embodiments disclosed herein reduces impedance and improves signal quality.

EXPERIMENTAL

Aspects of the present teachings can be further understood in light of the following examples, which should not be construed as limiting the scope of the present teachings in any way.

Example 1

Intracellular Recording of Action Potentials by Nanopillar Electroporation

The following example shows that vertical nanopillar electrodes can record both the extracellular and intracellular action potentials of cultured cardiomyocytes over a long period of time with excellent signal strength and quality. Moreover, it is possible to repeatedly switch between extracellular and intracellular recording by nano scale electroporation and resealing processes. Furthermore, vertical nanopillar electrodes can detect subtle changes in action potentials induced by drugs that target ion channels.

Vertically aligned nanopillar electrodes (FIG. 1a,b) can form tight junctions with mammalian cell membranes and can lower the impedance by orders of magnitude through localized electroporation, thus achieving excellent signal strength and quality in long-term and minimally invasive extracellular and intracellular recordings.

Materials and Methods

Chemicals and Reagents

Four-inch quartz wafers were purchased from Hoya Optics. Chromium etchant CR14 was sourced from Transene. All reagents used for cell culture, including gelatin, fibronectin, Claycomb medium, fetal bovine serum, norepinephrine, L-glutamine, penicillin and streptomycin, were purchased from Sigma-Aldrich, as well as ion channel drugs, nifedipine and tetraethylammonium. SEM sample preparation supplies such as glutaraldehyde, sodium cacodylate buffer and osmium tetroxide were bought from Ted Pella. RTV108 silicone glue was from Momentive.

Nanopillar Electrode Device Fabrication and Characterization

Figure 6:
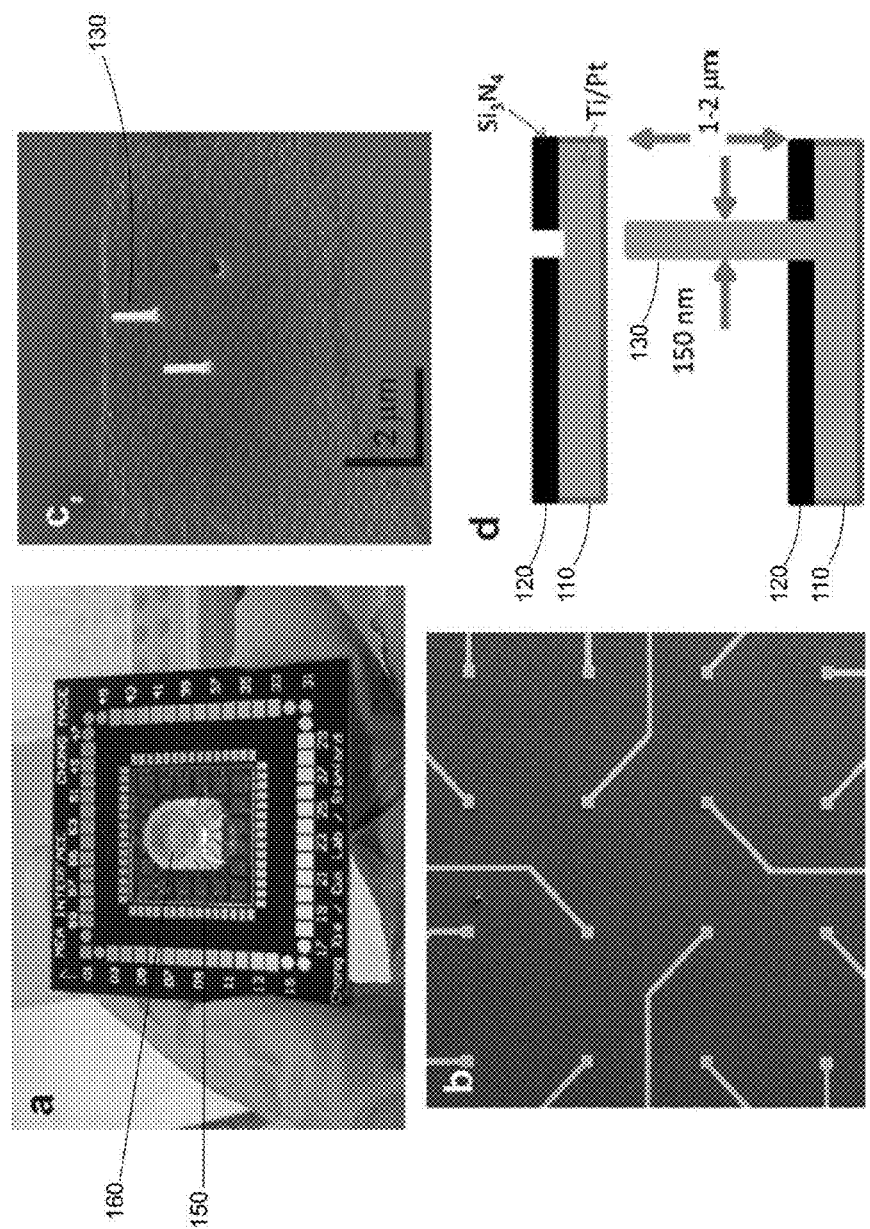
FIG. 6 shows a nanopillar electrode device.
Figure 10:
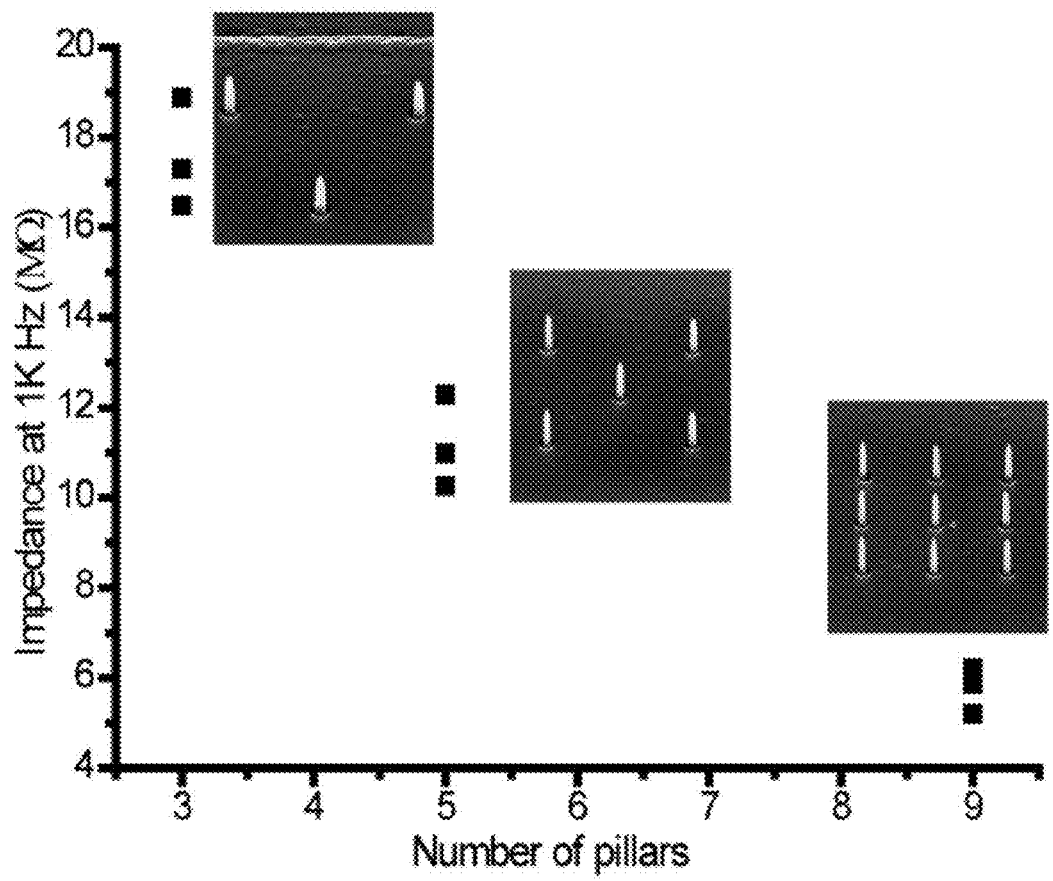
FIG. 10 shows electrical impedance measurements of the nanopillar electrode arrays. The electrical impedance of the nanopillar electrodes was measured with an Agilent B1500A parameter analyzer at 1 kHz frequency. Cell culture Claycomb medium was used as the electrolyte for the measurement. The impedance decreased as the number of nanopillar electrodes increased from 3 to 9 per array. This is expected as the conductive surface area is proportional with the number of nanopillar electrodes. For a 9-nanopillar electrode array, the impedance at 1 kHz is about 6 MΩ.

A four-inch quartz wafer was diced into 20×20 mm² pieces, and each piece was patterned with four-by-four electrode (Pt/Ti, 100 nm/10 nm) leads and pads using standard photolithography methods. The custom-designed electrode pattern is shown in FIG. 1a and FIG. 6a. The substrate surface was passivated with a 350 nm $Si_3N_4/SiO_2$ layer deposited by plasma-enhanced chemical vapor deposition. After coating with 5 nm chromium, a focused gallium ion beam was used to mill 250-nm-diameter holes through the insulation layer to reach the platinum pads underneath (FEI Strata DB 235). Vertical nanopillar electrodes were then created from the holes with focused ion beam (FIB)-assisted platinum and electrically connected with the platinum pads under the insulation layer. For each platinum pad, 1-10 nanopillar electrodes were constructed. Each nanopillar electrode was 1-2 µm long, with a diameter of 150-200 nm. After nanopillar electrode fabrication, the chromium layer was removed by CR14 so that the substrate was transparent, except for the electrode-covered areas. The electrical impedance of a finished chip in Claycomb culture medium was measured with an Agilent B1500A parameter analyzer, and was shown to decrease as the number of nanopillar electrodes increases (FIG. 10). A plastic chamber was glued onto the center of the chip using RTV108 silicone glue for cell culture purposes. The device was finished by mounting the chip on a custom-designed printed circuit board and electrically connecting it by wire bonding (FIG. 6).

HL-1 Cell Culture and Optical Imaging

The HL-1 cardiomyocyte cell line was obtained from the laboratory of William C. Claycomb at Louisiana State University. Before plating, the nanopillar electrode device was cleaned with detergent and deionized water, followed by 5 minutes of oxygen plasma treatment. The culture chamber was coated with 5 $\mu g$ $ml^{-1}$ fibronectin in 0.02% gelatin solution overnight to facilitate cell attachment (Claycomb et al. (1998) Proc. Natl. Acad. Sci. USA 95:2979-2984). HL-1 cells were then plated inside the chamber at a density of ~1×10⁵ cm⁻² and were maintained in the Claycomb medium supplemented with 10% fetal bovine serum, 0.1 mM norepinephrine, 2 mM L-glutamine and 100 U $ml^{-1}$ penicillin and 100 $\mu g$ $ml^{-1}$ streptomycin. The cells were maintained in a standard incubator at 37° C. and 5% $CO_2$. Medium was changed every 24 hours. A typical HL-1 cell culture reaches confluence 4-5 days after plating and exhibits spontaneous and synchronous beating, which can be observed on a Leica DM6000 inverted microscope. Fluorescent imaging of calcein dye was performed with a 470 nm excitation filter and a 525 nm emission filter.

SEM/FIB sample preparation. HL-1 cells cultured on the nanopillar electrodes were fixed with 2% glutaraldehyde and 4% paraformaldehyde in 0.1 M cacodylate buffer (pH 7.3), washed in the same buffer, and post-fixed with 1% osmium tetroxide. After washing twice in deionized water, the sample was dehydrated by successive exchanges with increasing concentrations of ethanol (50%, 70%, 90% and 100%). The sample in 100% ethanol was dried with liquid $CO_2$ in a critical point drier, which preserved the cell morphology during the drying step. Before SEM imaging, the sample was sputter-coated with a 2 nm gold layer to improve conductance. The sample was imaged using a FEI Strata 235B dual-beam SEM/FIB system that combined high-resolution SEM imaging and FIB milling. To expose the cell-nanopillar electrode interface, a cell-covered nanopillar electrode was first located under SEM, and FIB was used to carry out submicrometer vertical dissection at the desired locations.

Electrophysiology Measurement

A 60-channel voltage amplifier system (Multichannel System, MEA1060) was used to record HL-1 cells cultured on the nanopillar electrode arrays (nine nanopillars per array) after the cells started beating. Recording was performed in the same culture medium at 37° C. with an Ag/AgCl electrode in the medium as the reference electrode. The amplification was typically 110× for intracellular recording or 1,100× for extracellular recording, and the sampling rate was 5-20 kHz. The signal was filtered with a band-pass of 1 Hz-5 kHz. For electroporation, 20 biphasic pulses of 2.5 $V_{amp}$ were applied to a nanopillar electrode in a total time of 1 second. The recording system was blanked during the electroporation period. Electrophysiology recordings were resumed 20-40 seconds after electroporation to avoid amplifier saturation.

Results

HL-1 cells (a mouse cardiac muscle cell line; Claycomb et al., supra), cultured on nanopillar electrodes, show normal growth and exhibit spontaneous beating after reaching confluence. HL-1 cells were cultured around platinum nanopillar electrodes (length, 1.5 µm; diameter, 150 nm) on glass coverslips without any underlying electrodes to examine their health by means of optical microscopy. Live imaging demonstrated that the cardiomyocytes growing on the nanopillar electrodes had a morphology similar to those on planar areas during rhythmic beating (FIG. 1c). Scanning electron microscopy (SEM) after cell fixation revealed that the nanopillar electrodes were covered by the attached cell (FIG. 1d), a phenomenon similar to that observed previously in nanostructure-cell interactions (Hai et al., supra; Kim et al. (2007) J. Am. Chem. Soc. 129:7228-7229; Shalek et al. (2010) Proc. Natl. Acad. Sci. USA 107:1870-1875). To further inspect the cell-nanopillar electrode interface, we used focused ion beam (FIB) milling to expose the interface cross-section. Subsequent SEM imaging revealed that the nanopillar electrodes were engulfed tightly by the cell (FIG. 1e). Protrusions from the cells growing next to the nanopillar electrodes demonstrated a strong tendency to attach to the nanopillar electrodes (FIG. 1f), suggesting strong interactions between these electrodes and the cell membrane. Our findings agree with those of our previous study on the interaction between platinum nanopillars and primary cultured rat neurons (Xie et al. (2010) Nano Lett. 10:4020-4024).

Figure 2:
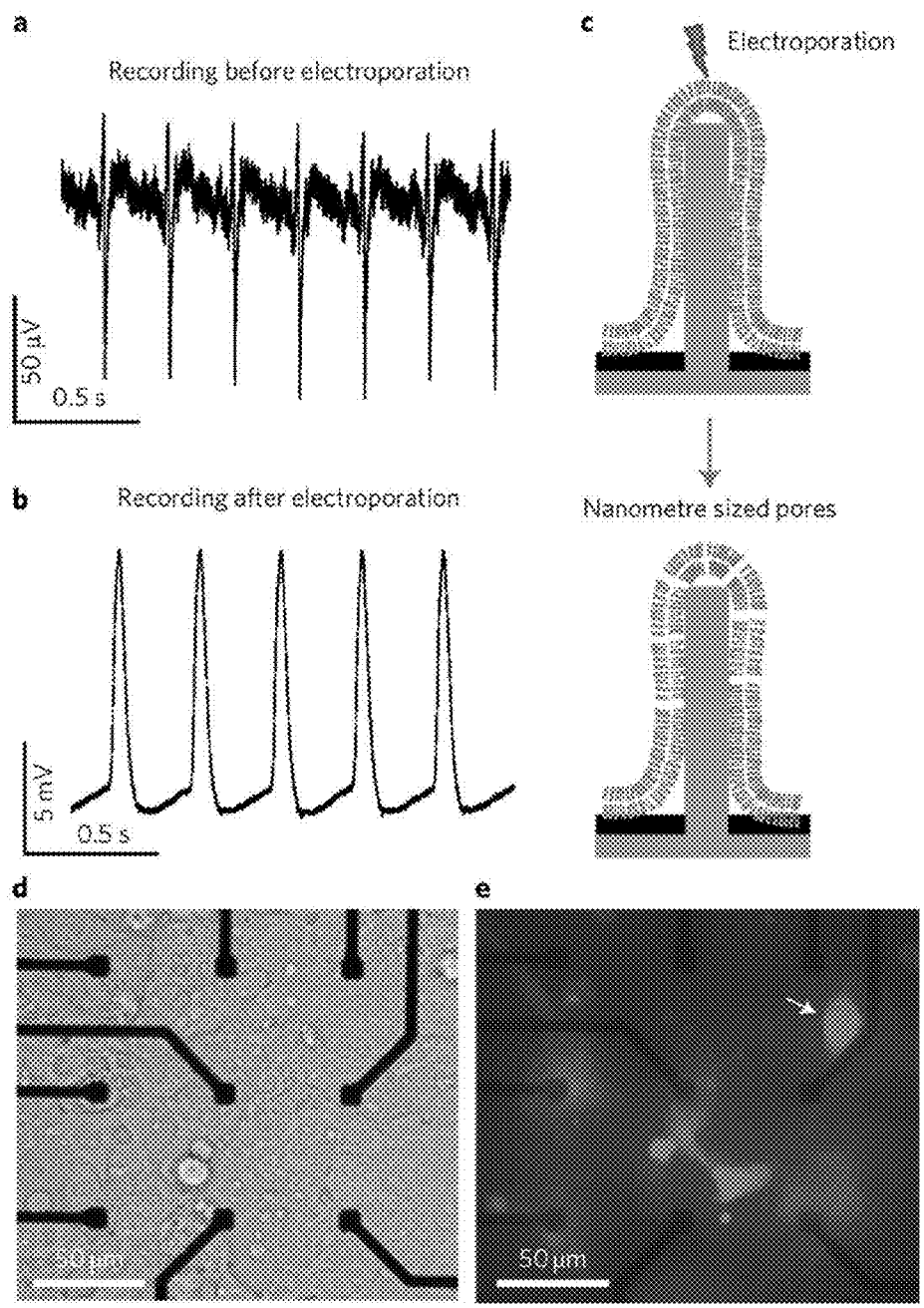
FIG. 2 shows recordings of action potentials of a single HL-1 cell before and after electroporation.

Devices assembled with the nanopillar electrode arrays (typically nine nanopillars per array with underlying electrical connections) were then used to record action potentials from HL-1 cardiomyocytes. FIG. 2a shows that the recorded action potential exhibits two signatures of extracellular recording: a spike with a shape that corresponds to the first derivative of the intracellular potential and an amplitude of ~100-200 µV. The peak-to-peak noise level is 30 µVpp and the signal-to-noise ratio is in the range 4.5-9. For comparison, a typical commercial multielectrode array registers a noise level of 40 µVpp for TiN electrodes with a diameter of 10 µm and 10 µVpp for a diameter of 30 µm, and an action potential signal strength of 100-500 µV. It is important to note that although the signal strength recorded by the nanopillar electrode arrays is similar to that measured by commercial planar multielectrode arrays, the surface area of a nanopillar electrode array (5-10 µm$^2$) is much smaller than that of a multielectrode array (400-2,500 µm$^2$)$^2$. Because of the capacitive coupling nature of a solid-state electrode, the detected signal strength directly correlates with the electrode area. Our observation suggests that tight engulfment of the nanopillar electrodes by the cell membrane results in good sealing at the interface and therefore compensates for the decreased electrode detection area.

A transient electroporation drastically improves the quality of the nanopillar electrode-recorded signal by lowering the impedance between the electrode and the cell interior. A high electric field can induce nanometer-sized pores in the cell membrane, as in the established in vitro technique that uses electroporation to introduce DNA or other molecules into cells (Zimmermann et al. (1974) Biophys. J. 14:881-899; Neumann et al. (1982) EMBO J. 1:841-845; Chang et al. (1990) Biophys. J. 58:1-12). Because the electrodes in this experiment are sharp (tip radius of <100 nm) and tightly coupled to the membrane, they can create a large electric field with a small voltage to transiently and locally increase the permeability of the cell membranes (FIG. 2c). FIG. 2b shows the recorded action potentials after the nanopillar electrodes deliver a train of 2.5 V, 200 µs biphasic pulses (20 pulses in 1 s) to an HL-1 cell. The recorded signal amplitude increases to 11.8 mV immediately after electroporation. The noise level of 30 µV$_{pp}$ is similar to that of extracellular recording levels, but the signal-to-noise ratio increases to 590 (FIG. 2b versus FIG. 2a). In comparison, a typical current-clamp recording has a noise level of 180 µVrms and signal strength of ~100 mV (Sakmann, B. & Neher, E. Single-Channel Recording, 2nd edn. (Springer, 2009)). Nanowire field-effect transistors typically have a noise level of 2-3 mV and signal of 60 mV (Tian et al. (2010) Science 329:830-834). In addition to this 100-fold increase in the signal-to-noise ratio, our recorded action potentials have the following intracellular attributes: a triangular shape and action potential duration at 50% of the maximum (APD50) of 30.8±0.2 ms.

Immediately following each action potential, a clear refractory period is visible, which is characterized by a slow smooth transition from the maximum diastolic potential to the threshold for the initiation of the next action potential. The recorded action potential shape agrees well with patch-clamp recording of HL-1 cells (Salami et al. (2002) J. Physiol. 545:81-92). A total of 32 devices with at least two cultures on each device were tested, and intracellular recording after electroporation was observed for every culture on every device.

Figure 7:
FIG. 7 shows an enhanced contrast and zoomed-in image of FIG. 2e showing that the electroporated cell extends to the nanopillar electrode site.

Electroporation was confirmed by delivering membrane-impermeable calcein dye into the HL-1 cells with the same pulse sequence used to induce intracellular recording (FIG. 2d,e). Of the nine platinum pads shown in FIG. 2d (the nanopillar electrodes on the pads are not visible in this image, which was taken by an inverted microscope), the six pads in the second and third rows have nanopillar electrode arrays. To serve as a control, the three pads in the topmost row had milled holes to expose the platinum pads, but no nanopillar electrodes. As shown in FIG. 2e, although the same pulse sequence was applied to all nine platinum pads, only those cells on nanopillar electrode arrays experienced electroporation and took up the dye. Notably, not all the permeabilized cells were located exactly on top of the nanopillar electrodes. The cell indicated by the white arrow in FIG. 2e is not directly over the electrode, but, like the cell shown in FIG. 1f, its protrusion extends to the nearest nanopillar electrode site (as can be seen in the image with higher contrast in FIG. 7). It is important to note that nanopillar electrode electroporation causes minimal cell damage because a relatively low voltage is applied, and electroporation happens only in the membrane immediately surrounding each electrode, which has an area of ~1 µm$^2$ (compared to the overall cell membrane area of ~1,000 µm$^2$).

Figure 3:
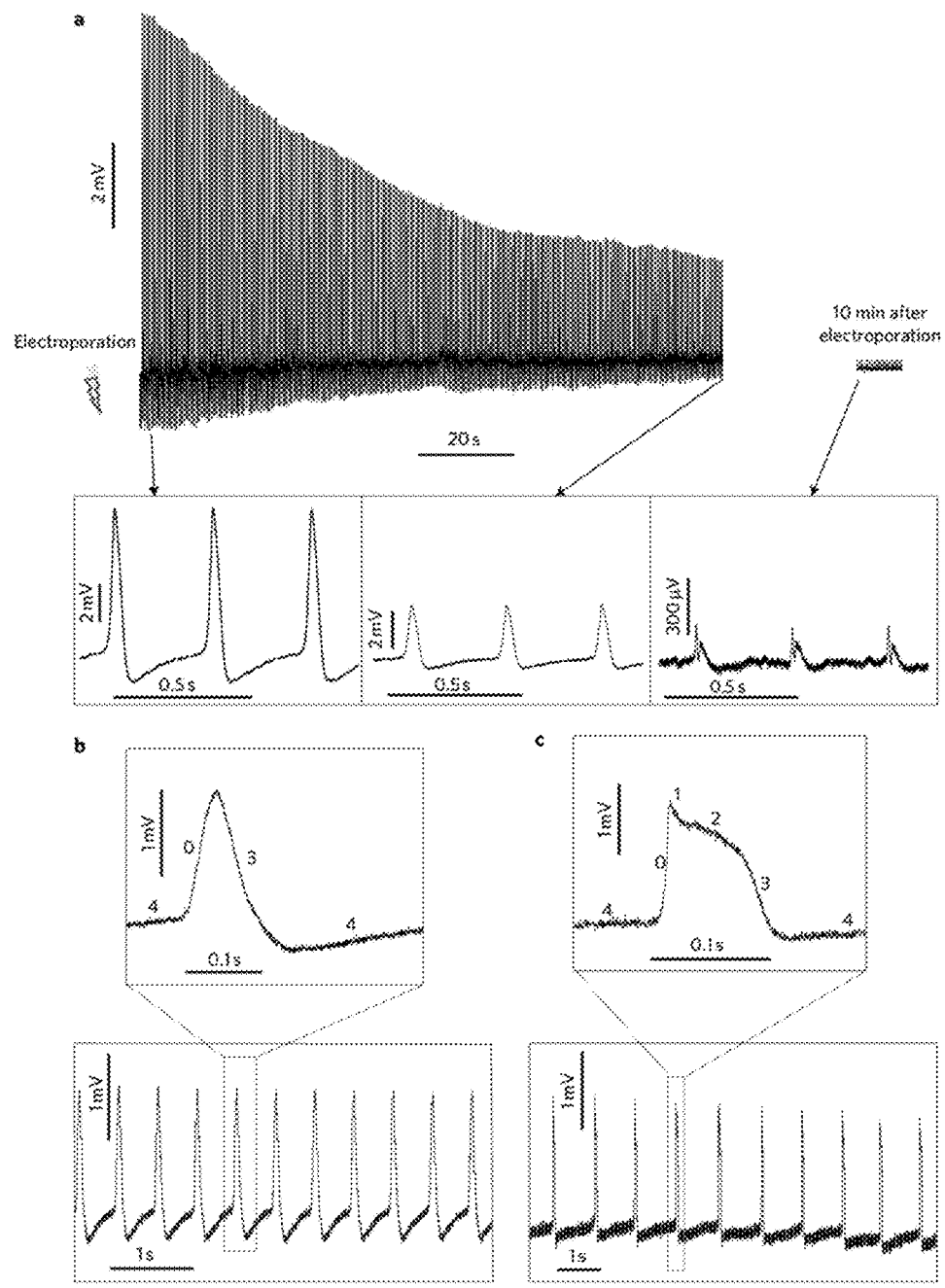
FIG. 3 shows minimally invasive intracellular measurement of action potentials with high precision.
Figure 8:
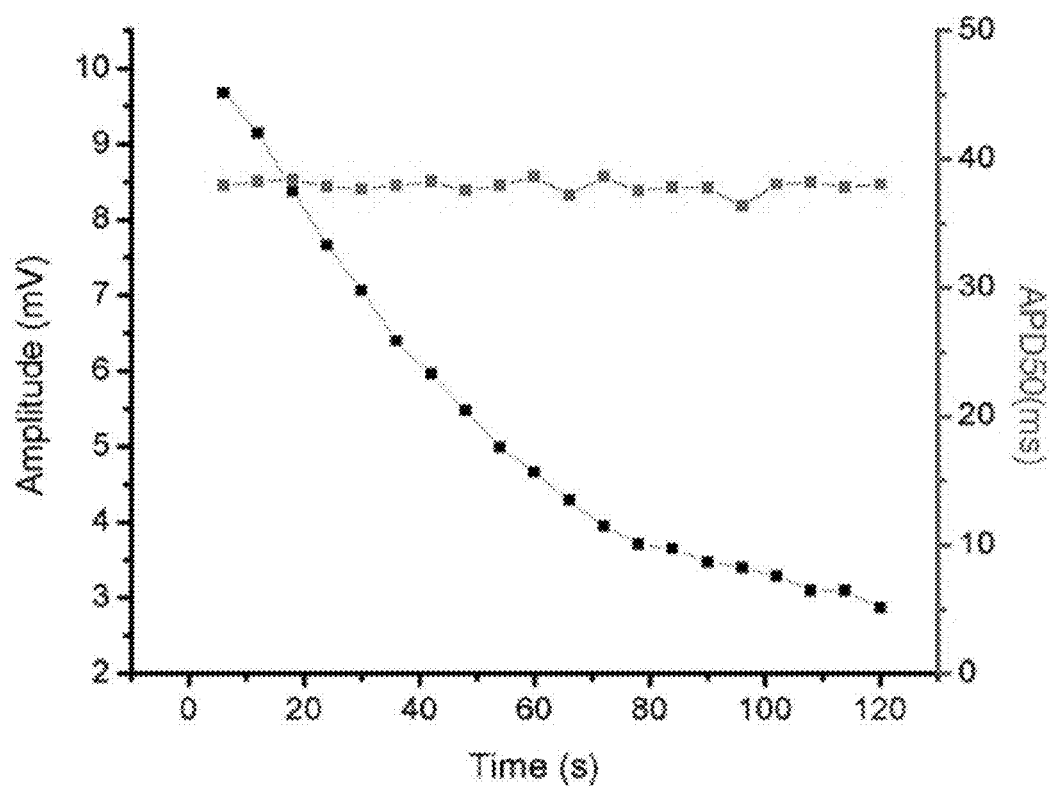
FIG. 8 shows time evolution of the measured action potential amplitude and duration at 50% maximum (APD50). 120 seconds after electroporation, the measured amplitude decayed significantly to about 30% of the maximum. On the other hand, the APD50 remained constant during this period.

Nanopillar electrode intracellular recording following electroporation is not only minimally invasive but also provides details of HL-1 action potentials with high resolution. We observe that electroporation-generated pores seal within several minutes. FIG. 3a shows a 10 minute recording immediately after electroporation. The amplitude of the recorded action potential decays to 30% of its original amplitude after 120 seconds. However, during this period, the APD50 remains relatively constant (FIG. 8). After 10 minutes, the recorded signal decays to ~200 µV and transitions back to extracellular features. The timescale for pore sealing is comparable to that of the recovery reported after the electroporation of bulk suspended cells (Tovar et al. (1992) Am. J. Physiol. 263, H1128-H1136). This observation further confirms that the recorded signal improvement is a direct result of electroporation. In addition, the high-resolution recording allows the possibility of distinguishing different types of cells in the same culture based on the shapes of their action potentials. For example, the action potential shown in FIG. 3b resembles that of pacemaker cells, whereas the action potential shown in FIG. 3c resembles that of non-pacemaker cells. The pacemaker cells have three phases with symmetric rising and falling edges. The slow rising edge is phase 0, attributed to increased inward Ca$^{2+}$ conductance, and the falling edge is phase 3, caused by K$^+$ channel opening. In contrast, all five phases are present in non-pacemaker cells. The five phases represent, respectively, the opening of fast Na$^+$ channels (depolarization phase 0), the transient outwards K$^+$ channels (short repolarization phase 1), the slow inward Ca$^{2+}$ channels (plateau phase 2) and the K$^+$ channels (depolarization phase 3 and resting potential phase 4).

Figure 4:
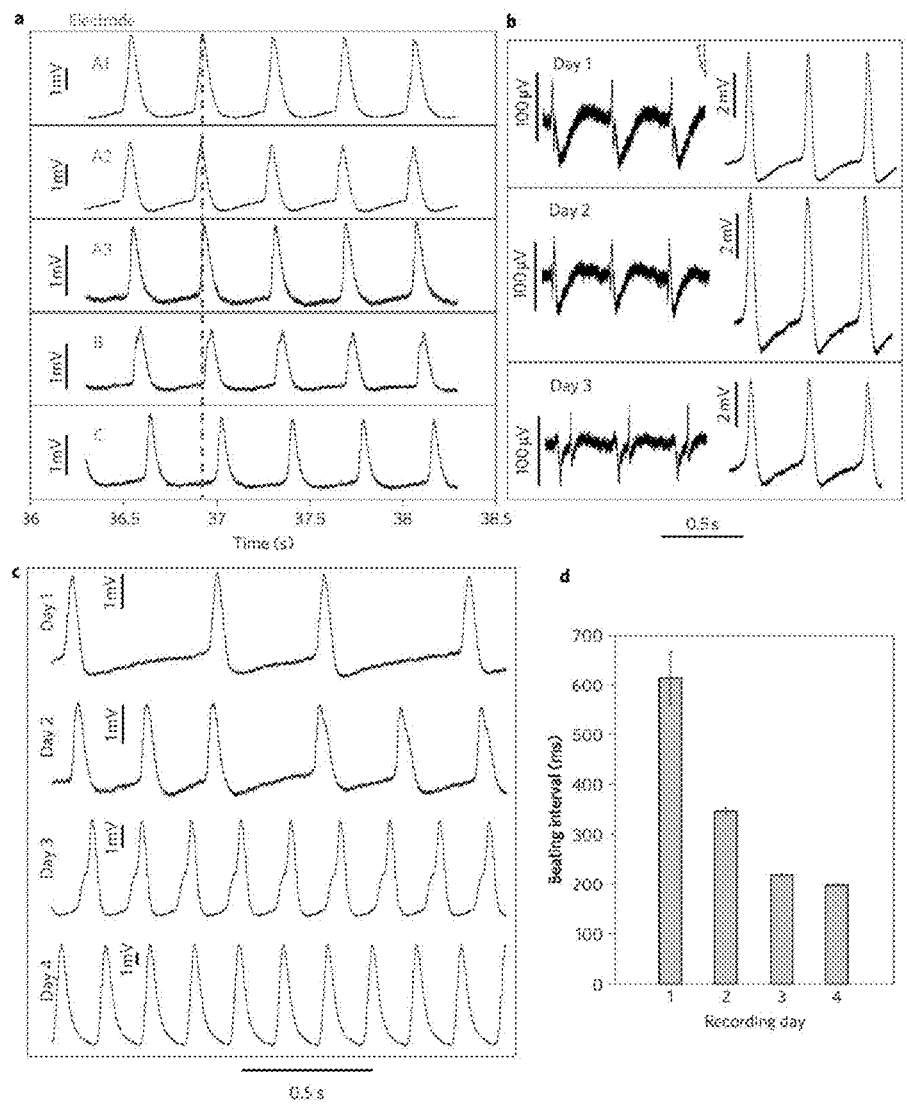
FIG. 4 shows parallel intracellular recording of multiple cells and the evolution of action potentials over consecutive days for single cells.

The high-throughput and minimally invasive character of nanopillar electrode intracellular recording allows repetitive recording on multiple cells, in parallel, over several consecutive days. FIG. 4a shows simultaneous intracellular recording with five different electrodes on the same culture. Electrodes A1, A2 and A3 are within 40 µm of one another, and electrodes B and C are separated by ~400 µm from one another and from electrodes A1-A3. We observe that cells on electrodes A1-A3 undergo synchronized beating, but there are time delays between cells on electrodes B and C. This is probably because different cell patches in the culture beat with delays before they reach confluence and start synchronized beating.

FIG. 4b shows recordings from a cell in a mature culture on three consecutive days before and after each electroporation. Although the amplitude of the recorded signal varies, the recorded action potential shape, APD50 and frequency remain relatively constant over the three-day period. In contrast, an HL-1 cell in a developing culture exhibits significant changes in both beating interval and action potential amplitude over the course of four days (FIG. 4c). The cell transitions from arrhythmic to rhythmic beating with increasing frequency (beating interval of 613.2±53.6 ms on day 1 and 197.8±0.5 ms on day 4; FIG. 4d), together with an increase in recorded maximum action potential amplitude (2.76 mV on day 1 and 9.49 mV on day 4).

Figure 5:
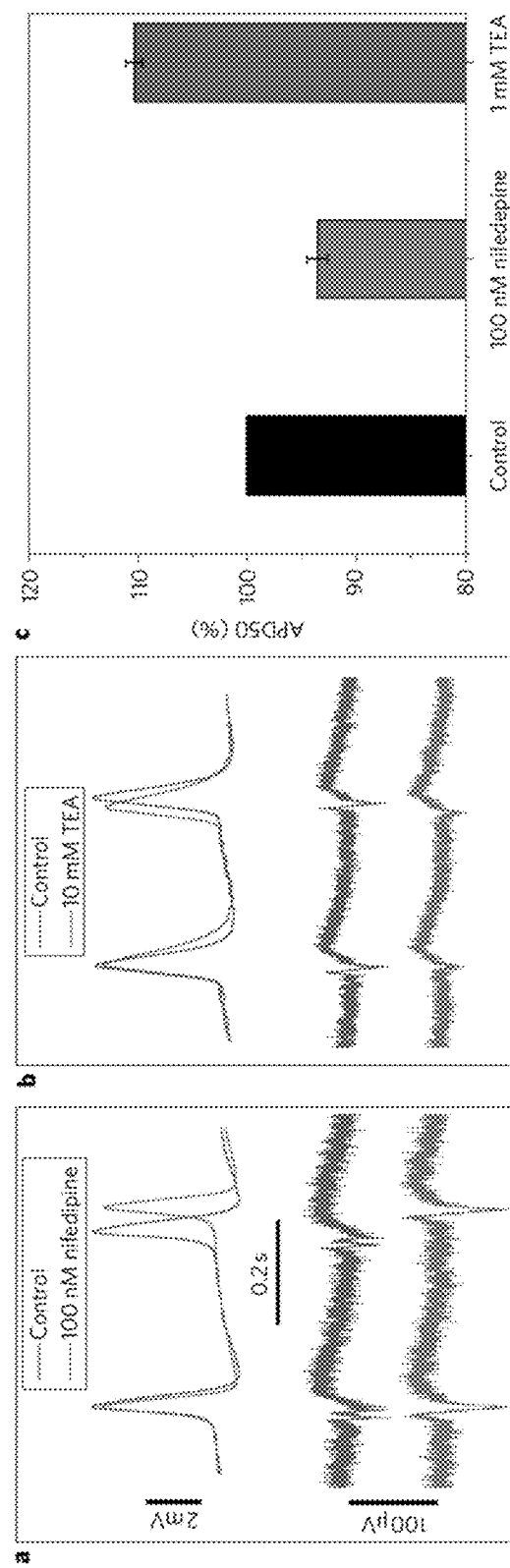
FIG. 5 shows the effect of ion-channel blocking drugs on HL-1 cells.
Figure 9:
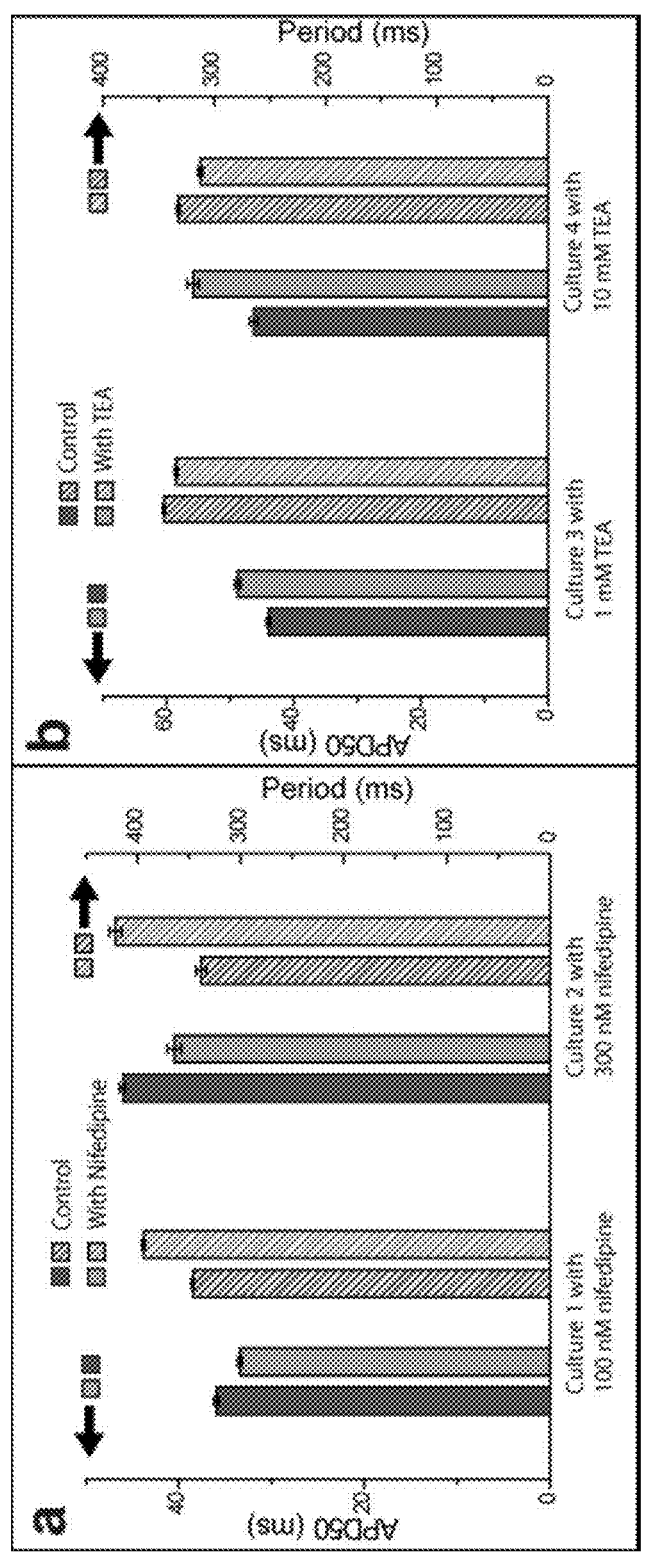
FIG. 9 shows the effect of nifedipine and tetraethylammonium on HL-1 action potentials measured by nanopillar electrodes.

The highly detailed recording by the nanopillar electrodes after electroporation also allows us to examine the effect of ion-channel drugs on HL-1 action potentials. We demonstrated this capability as an example of potential drug screening applications by testing nifedipine (a $Ca^{2+}$ channel blocker that shortens action potentials) and tetraethylammonium (a $K^+$ channel blocker that lengthens action potentials; Zipes, D. P. & Jalife, J. Cardiac Electrophysiology: From Cell to Bedside, 4th edn (Saunders, 2004); Catterall (1988) Science 242:50-61; Choi (1991) Proc. Natl. Acad. Sci. USA 88:5092-5095). For control experiments, we electroporated the cells to record action potentials in the absence of drugs. After the cells had recovered for a few hours, nifedipine or tetraethyl-ammonium of different concentrations was added to the culture medium and the cultures incubated for 10 minutes. Subsequently, another electroporation was applied to record the action potentials of the drug-treated cells. As shown in FIG. 5, nanopillar electroporation recording revealed subtle changes in the shape, duration and frequency of the action potentials. Treatment with 100 nM nifedipine clearly decreases the duration of the action potential (quantified by APD50) and increases the period. Treatment with 10 mM tetraethylammonium shows the opposite effect, increasing APD50 and decreasing the period. For either drug, the effects on APD50 and action potential period are enhanced with increasing concentration (FIG. 9). Although the shapes of recorded action potentials vary from cell to cell, the drug effect was reliably detected because we were taking recordings from the same cell before and after drug application (Tables 1 and 2).

With the advantages of long-term measurement, high sensitivity and minimal invasiveness, vertical nanopillar electrode recording has many potential applications, including basic biomedical research (for example, studying the electrophysiology of different domains within single cells or groups of cells, and investigating the evolution of individual cell electrophysiology during cell development) and pharmaceutical screening. Arrays of nanopillar electrodes can be used to mechanically pin down mammalian cells (Xie et al. (2010) Nano Lett. 10:4020-4024), which should allow targeted cells to be measured without chemical or biological labels.

TABLE 1

Decrease in APD50 of 4 different cells in 3 different cultures after administration of 100 nM nifedepine recorded by nanopillar electrodes. Even though there is large variation in APD50 among different cells in different cultures, the change in APD50 is consistent because we are comparing the APD50 before and after drug administration on the same cell.

| 100 nM nifedepine | APD50 before drug (ms) | APD50 after drug (ms) | APD50 change (%) |
| --- | --- | --- | --- |
| Cell1 | 44.25 | 41.52 | 93.8 |
| Cell2 | 46.36 | 43.40 | 93.6 |
| Cell3 | 43.52 | 40.92 | 94.0 |
| Cell4 | 35.94 | 33.39 | 92.9 |

TABLE 2

Increase in APD50 of 4 different cells in 3 different cultures after administration of 1 mM tetraethylammonium recorded by nanopillar electrodes.

| 1 mM tetraethylammonium | APD50 before drug (ms) | APD50 after drug (ms) | APD50 change (%) |
| --- | --- | --- | --- |
| Cell1 | 43.92 | 48.78 | 111.1 |
| Cell2 | 50.01 | 54.93 | 109.8 |

TABLE 2-continued

Increase in APD50 of 4 different cells in 3 different cultures after administration of 1 mM tetraethylammonium recorded by nanopillar electrodes.

| 1 mM tetraethylammonium | APD50 before drug (ms) | APD50 after drug (ms) | APD50 change (%) |
| --- | --- | --- | --- |
| Cell3 | 45.96 | 50.54 | 109.9 |
| Cell4 | 41.38 | 45.74 | 110.5 |

Example 2

Nanotube Electrodes for Highly Sensitive Measurement of Membrane Potential and Repair The following example shows that iridium oxide nanotube electrodes record action potentials with amplitudes up to an order of magnitude larger and access durations 1-2 orders of magnitude longer than those recorded by solid gold nanopillars of the same size. This high fidelity and sensitive recording also enables us to monitor plasma membrane repair after local electroporation, identify two distinct repair dynamics and study single pore sealing with millisecond temporal resolution. Together with the advantages of easy multiplexing and recording throughout cultures' lifespan, the iridium oxide nanotube electrodes afford a powerful tool for long-term electrophysiology study of cell development as well as membrane repair biology.

Materials and Methods

Iridium Oxide Nanotube Fabrication.

IrOx nanotube electrode arrays were fabricated in two steps. The first step defined the underlying electrical connections and the second step created the IrOx nanotubes. Pt pads and lines were defined by photolithography, Pt deposition and liftoff. A layer of $Si_3N_4/SiO_2$ was deposited for electrical insulation. Arrays of three-by-three nanoholes were defined on the $Si_3N_4/SiO_2$ above the Pt pads by electron beam lithography and etching. IrOx nanotubes were then anodically electrodeposited on Pt pads with the $Si_3N_4/SiO_2$ and electron beam resist as templates. Electroplating bath contained iridium(IV) chloride, oxalic acid and potassium carbonate (Sigma-Alrich). Finally, resist was removed to reveal the nanotube arrays.

Cardiomyocyte Culture and Electron Microscopy.

HL-1 cardiomyocytes were cultured in supplemented Claycomb medium on the substrates coated with fibronectin in gelatin solution. Electron microscopy sample was prepared by fixation, $OsO_4$ staining, dehydration with graded ethanol series, $CO_2$ critical point drying and metal deposition. Cells were "unroofed" by brief sonication pulses during electron microscopy preparation.

Electrophysiology Recording.

After the HL-1 cells exhibited spontaneous beating (usually four days after plating), the chip was connected to a 60-channel voltage amplifier (MEA1060-Inv, Multi Channel Systems) for recordings at 5 kHz sampling rate. The recordings were performed in Claycomb culture medium at room temperature. The electroporation pulse consisted of 100 consecutive biphasic and symmetric square pulses, each with 400 µs period and 3.5 V amplitude. Recordings were resumed ~10 s after electroporation to avoid amplifier saturation. Nanotube electrode devices were reused after multiple cultures by trypsinization, DI water clean and oxygen plasma. Whole-cell current clamp was performed at room temperature using with Axon Multiclamp 700B amplifier (Molecular Devices). Patch pipettes had resistance of 2-4 MΩ. Intracellular solution contained (in mM): 140 KCl, 10 NaCl, 10 HEPEs, and 1 EGTA (pH 7.3) and extracellular batch solution was Claycomb medium. Data was sampled at 10 kHz and low-pass filtered at 3 kHz by Axon Digidata 1440A (Molecular Devices).

Results

Figure 11:
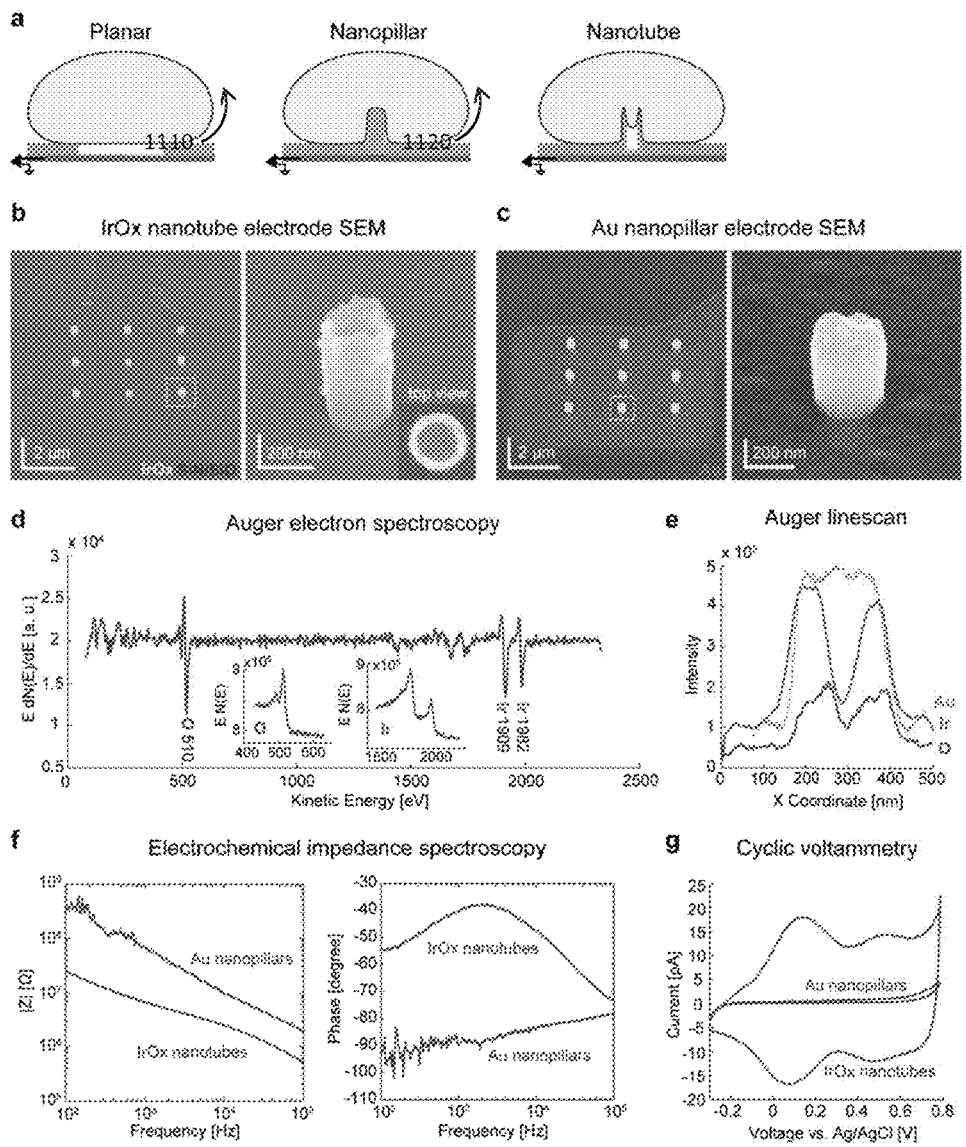
FIG. 11 provides a characterization of electrodeposited vertical iridium oxide nanotubes.
Figure 15:
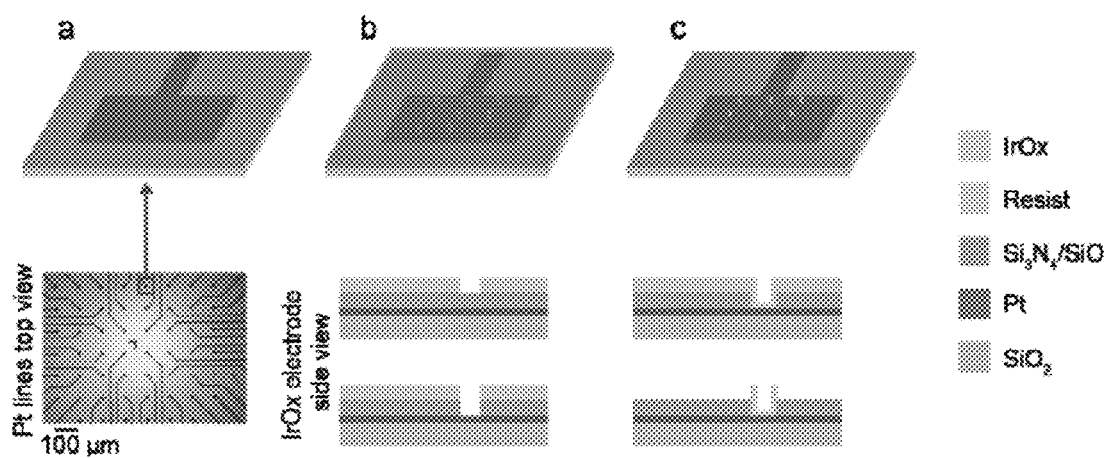
FIG. 15 is a set of schematics of iridium oxide nanotube electrode fabrication.

We fabricated our IrOx nanotube electrode arrays in two steps. The first step defined the underlying Pt lines for electrical connection and insulated them with $Si_3N_4/SiO_2$; and the second step created the IrOx nanotubes by electron beam lithography and electrodeposition with $Si_3N_4/SiO_2$/resist nanoholes as the template. Unlike electrodeposition of metals yielding nanopillars, electrodeposition of IrOx yields nanotubes (Mafakheri, E. et al. Electroanal 23, 2429-2437 (2011)). FIG. 11b shows a three-by-three array of vertical IrOx nanotube electrodes on top of a Pt pad (FIG. 15). The small array footprint of 4×4 μm² allows single cell recording. Scanning electron microscopy confirmed the nanotube geometry. The hollow core of the IrOx nanotubes is obvious from the side and top views. The nanotubes are uniform with 181±3 nm diameter (peak-to-peak) and 40±3 nm wall thickness (n=30), and their height is ~500 nm and can be tuned by template thickness and electrodeposition duration. The nanotubes are sealed on their bottom ends by a layer of IrOx contacting the Pt pads, and at the same time a layer of $Si_3N_4/SiO_2$ provides electrical insulation to the rest of the Pt area so that only the IrOx interact with cells electrically. In comparison, Au electrodeposited in the same template yielded solid nanopillars (FIG. 11c). An Auger electron spectrum of the nanotube shows characteristic peaks for oxygen and iridium and confirms that the nanotubes are made of IrOx (FIG. 11d). Elemental analysis line scans of the nanotubes along their diameter shows the spatial distribution of both elements (blue and red lines in FIG. 11e). The spatial overlap of the oxygen and iridium spectra further indicates the uniformity of chemical composition. In comparison, line scan of an electrodeposited Au nanopillar shows a flat top rather than two peaks (green line in FIG. 11e).

Electrochemical studies reveal that IrOx nanotube electrodes have lower impedance and a higher charge storage capacity than Au nanopillars of the same surface area. Electrochemical impedance spectroscopy shows that the impedance of IrOx nanotubes ($|Z|=5.8\pm1.1$ MΩ at 1 kHz, n=9) is more than an order of magnitude smaller than that of Au nanopillars ($|Z|=86.9\pm22.0$ MΩ at 1 kHz, n=5) in phosphate buffered saline (FIG. 11f). Phase scan indicates that IrOx nanotubes behave as parallel capacitor-resistor circuits while Au nanopillars with a −90° phase behave similar to perfectly capacitive electrodes. Cyclic voltammetry also confirms that IrOx nanotubes process a larger charge storage capability than Au nanopillars (FIG. 11g). The total charge storage capacity of IrOx nanotubes is 30.3±1.6 mC/cm² (n=11), which is similar to that of electrodeposited IrOx film and more than 40 times larger than the capacity of Au nanopillars (0.69±0.07 mC/cm², n=10). These measurements indicate that IrOx nanotubes would be superior recording and stimulation electrodes than Au nanopillars.

Figure 12:
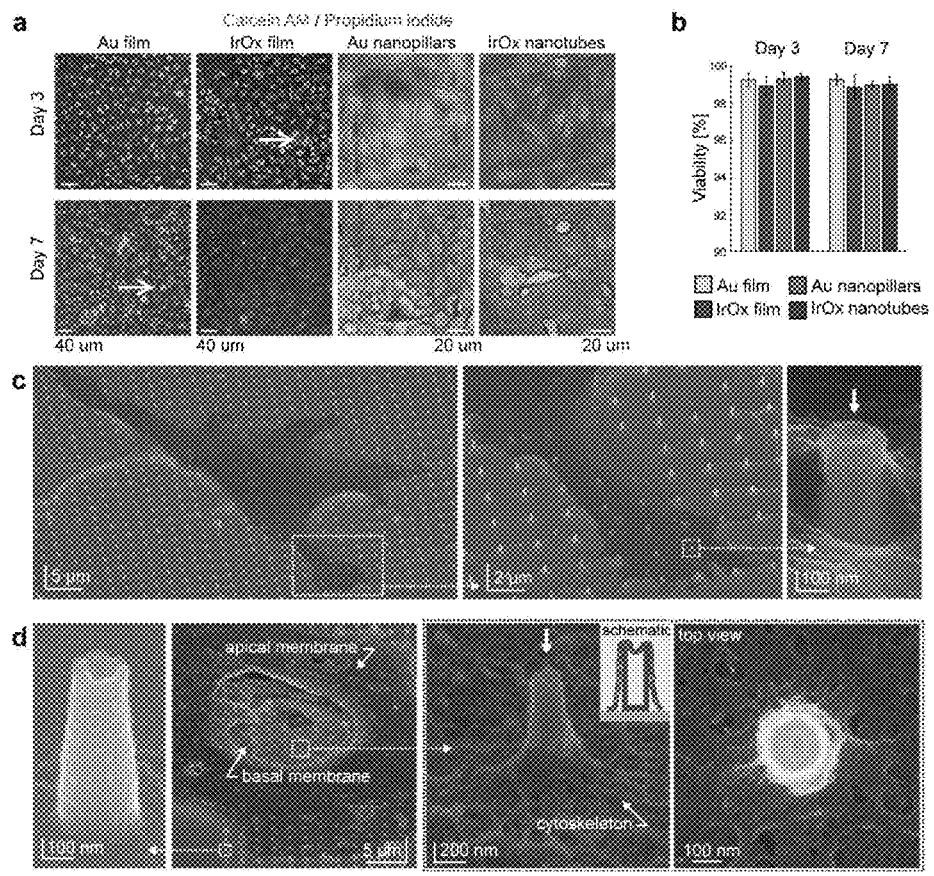
FIG. 12 shows rat cardiomyocytes interfacing with the vertical iridium oxide nanotube arrays.

After analyzing the physical properties of the IrOx nanotubes, we cultured HL-1 rat cardiomyocytes on large arrays of nanotubes to study cell-nanotube interactions. FIG. 12a shows cardiomyocytes after 3 or 7 days of culture on Au film (20 nm thickness), Au nanopillar arrays (750 nm height, 180 nm diameter, 2 μm spacing on 20 nm Au film), IrOx film (30 nm thickness on 20 nm Au film) and IrOx nanotube arrays (750 nm height, 180 nm diameter, 40 nm thickness, 2 μm spacing on 20 nm Au film). All substrate surface was coated with fibronectin in gelatin solution for cell adhesion and no other surface functionalization was performed to enhance cell membrane adhesion to the electrodes or facilitate electrode penetration into the cell bodies. To confirm the cell viability, we stained live cells with calcein (green) and dead ones with propidium iodide (red) in FIG. 12b. We found no distinction among cell viability on day 3 and 7 on all four substrates (n>1,400 cells in each data bar).

To further explore cell-nanotube interactions, we conducted scanning electron microscopy and found that cardiomyocytes engulf the vertical nanotubes and extend their plasma membrane into the nanotubes. This tight interaction is most easily observed at the cell edges, where the cell thickness is smaller than the nanotube height (FIG. 12c). Even the apical plasma membrane extends into the nanotubes (FIG. 12c arrow). To further study the interaction between the basal membrane and the nanotubes at the cell center, we removed the apical membrane and the cell nucleus by a brief sonication. FIG. 12d shows that the cytoskeleton of the basal membrane wraps around the vertical nanotubes like a dented tent with the nanotubes as posts. Most importantly, the basal plasma membrane protrudes into the nanotube (FIG. 12d). The sonication process occasionally detached some cardiomyocytes from the substrate. In this scenario, some nanotubes were unplanted from the surface and remained embedded in the detached cells. All of the above observations suggest a tight cell-nanotube interaction.

Figure 13:
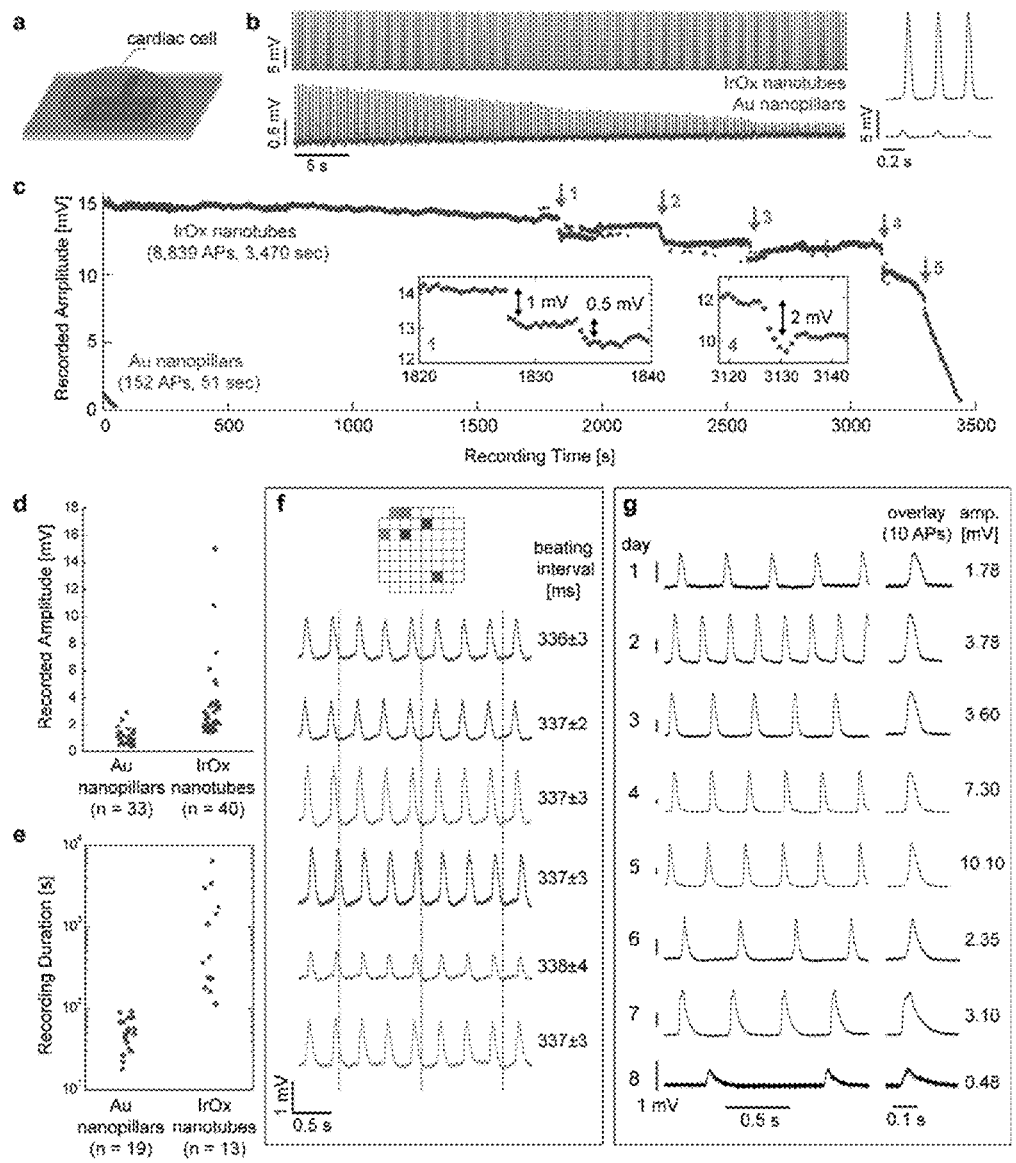
FIG. 13 provides an intracellular recording of cardiomyocyte action potentials by iridium oxide nanotube electrodes.

We then performed whole-cell intracellular recording of cardiomyocyte action potential with our IrOx nanotube electrodes (FIG. 13a) and measured not only larger amplitude but also orders of magnitude longer access durations than Au nanopillar recording. After local electroporation, the nanotube gained electrical access to the cell interior and recorded up to 15 mV action potentials (FIG. 13b). The beating interval remained unchanged before and after electroporation (percentage change is $((-0.51\pm1.45)$ %, n=22). The recorded intracellular signal decayed to 20% of its initial amplitude after a long duration of 3,470 s (8,839 action potentials) (FIG. 13c). In comparison, the intracellular signal recorded by Au nanopillars had an initial amplitude of only 1.2 mV and decayed with a short duration of 51 s (152 action potentials) (FIG. 13b and c). Measurements over many cells confirmed the superiority of IrOx nanotube recording. For the signal amplitude comparison, we restricted to cells that had been beating ~3 Hz for at least two days since the recorded amplitude and beating interval vary depending on cell culture age. The initial action potentials recorded by the IrOx nanotube electrodes (n=40) were up to an order of magnitude larger than that recorded by Au nanopillars (n=33). The IrOx nanotubes (n=13) also offer one or two order of magnitude longer intracellular access duration after electroporation than Au nanopillars (n=19) and our previous demonstrated Pt nanopillars.

Figure 16:
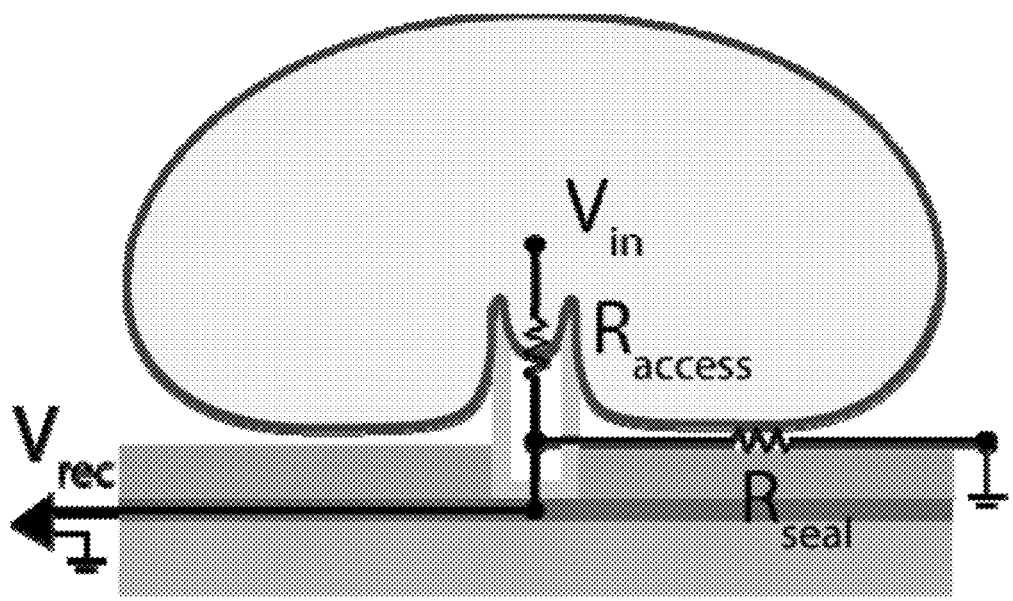
FIG. 16 is a simplified circuit model to illustrate the relationship between recorded potential and the actual membrane potential.

IrOx nanotubes are also robust electrodes that offer parallel recording as well as multiple-day monitoring of single cells. Since the IrOx nanotubes are built upon planar electrode array architecture, they can perform simultaneous recording of multiple cells in a culture. FIG. 13f shows a recording by six different electrodes on an 8×8 array chip with 100 μm separation between adjacent electrodes. The identical beating interval reveals that the whole culture underwent synchronized beating while the phase delay among different cells reveals how action potentials propagated in the culture. Furthermore, our IrOx nanotube electrodes can monitor the action potential evolution in the same cell over eight consecutive days (FIG. 13g), which is the lifespan of the culture. Overlays of 10 consecutively action potentials at each day show that the recordings were consistent. The initial increase in recorded action positional amplitude and frequency reflects culture maturation while the subsequent decrease of amplitude and frequency reflects culture ageing. In addition, FIG. 16 shows the six consecutive day recording by the same electrode in the following culture, demonstrating that the IrOx nanotubes electrodes are robust for repeated recordings.

The improvements in recorded signal amplitude and intracellular access durations enable IrOx nanotube electrodes for highly sensitive monitoring of plasma membrane repair in cardiomyocytes. Plasma membrane damage occurs frequently in skeletal and cardiac cells due to their mechanical activity, and failure in membrane repair could lead to cell death and muscular dystrophy. One of the most common methods to study plasma membrane repair relies on measuring the uptake of fluorescent dyes upon local membrane damage, but such method suffers several drawbacks including low sensitivity, poor temporal resolution (seconds to tens of seconds) and dye endocytosis. A recent report used gold-mushroom microelectrodes to locally electroporate snail neurons and a second patch-clamp electrode to measure the change of membrane resistance as a mean of monitoring membrane repair.

Figure 14:
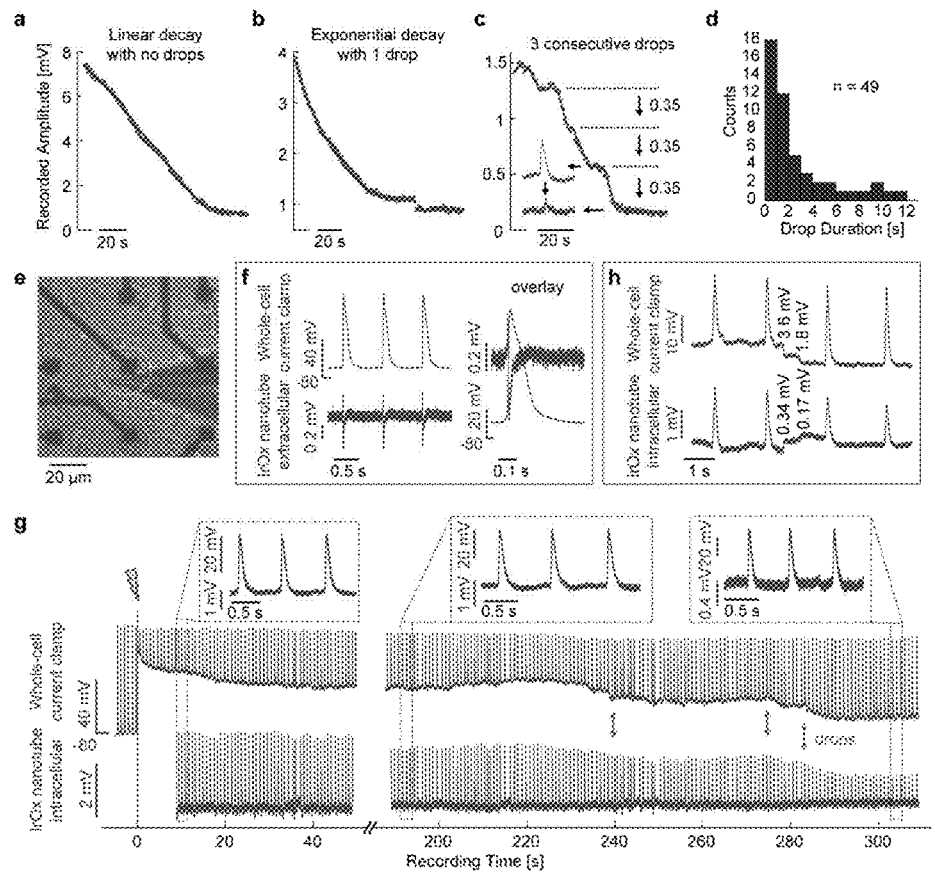
FIG. 14 shows membrane repair as measured by iridium oxide nanotube electrodes and verification by simultaneous patch clamp recording.

Here we show that IrOx nanotube electrodes achieve both local membrane electroporation and monitoring membrane resealing dynamics with high signal sensitivity and millisecond temporal resolution. After local electroporation, the measured action potential amplitudes decayed continuously in either linear or exponential fashion, or experienced discontinuous step drops (abrupt decays in recorded amplitude) accompanied by plateaus (defined as constant amplitude for at least 20 s). FIG. 14a and b illustrate a linear decay with a rate of $-0.07$ mV s$^{-1}$ and an exponential decay with a 40 s half time, respectively. The amplitude in FIG. 14b recording reached a plateau and underwent a step drop. FIG. 14c displays three consecutive step drops of the same amplitude of 0.35 mV. As the recorded amplitude is linearly proportional to membrane pore conductance after electroporation, the similar amplitude drops in FIG. 14c suggests the sudden sealing of three pores of similar sizes. The last drop was a transition from intracellular to extracellular recording (FIG. 14c inset). However, the step drops were often of different values in the same cell, indicating that the closing pores had different areas. For example, FIG. 13c show six drops with 0.5, 1, 1.5, and 2 mV amplitudes. This distribution of drop amplitudes agrees with a rapid-freeze electron microscopy study of circular pores in human red blood cells that shows a variable pore diameter of 20-100 nm after electroporation. FIG. 14d quantifies the drop duration (time difference between two adjacent plateau endpoints) and reveals that half of the drops occurred in less than 2 s (n=49).

The continuous decays and the discontinuous drops are indicative of two different membrane sealing mechanisms in cardiomyocytes. In fact, two membrane sealing hypotheses exist for nucleated cells. One is facilitated lipid self-resealing and the other is patch fusion with plasma membrane. The continuous character of our recorded linear and exponential decays agrees with the first hypothesis and the abrupt step drops agree with second one. We performed statistics on the occurrence frequency of different decays in our experiment. Out of more than a hundred recordings, continuous decay dominated (n=68), followed by continuous decay with step drops (n=20) and plateau with drops (n=17).

Finally, we verified our IrOx nanotube electrode recording by simultaneous whole-cell current clamp recording on the same cells. We patched a cardiomyocyte that resided on top of the IrOx nanotubes (FIG. 14e) and exhibited spontaneous contraction. Before any electroporation, the patch clamp recorded a train of spontaneous action potentials with a $-80$ mV resting membrane potential while the IrOx nanotubes registered extracellular spikes (FIG. 14f). After sending voltage pulses through the IrOx nanotubes, we observed elevated resting membrane potential by the patch-clamp recording (FIG. 14g), indicating cell membrane electroporation. As time progressed, the peak potential measured by the whole-cell patch clamp remained almost constant while the resting membrane gradually decreased through continuous decays and discontinuous drops and eventually returned to the pre-electroporation level. As expected, the IrOx nanotubes recorded intracellular potentials that have waveforms identical to the ones recorded by the whole-cell current clamp (FIG. 14g). The sudden drops of the resting membrane potential in the whole-cell current clamp were faithfully detected as sudden amplitude changes by the IrOx nanotubes (FIG. 14h). The exact correspondence between the IrOx nanotube recording and the patch clamp recording confirms that the membrane pores were highly localized around the nanotube electrodes. FIG. 14h further illustrates that drops as fast as 20 ms can be faithfully recorded, demonstrating that nanopillar electrical recording has a much superior time resolution in monitoring membrane repair than fluorescent dyes (1-10 s resolution). Note that the amplifier for the IrOx recording has a high-pass filter of $\sim 0.01$ Hz and therefore did not register DC level of the action potentials (Multi Channel Systems).

Nanotube Geometry Measurement.

50×50 nanohole arrays, each in 100×100 μm$^2$ area, were defined by electron beam lithography on ZEP520 resist on coverslips without any underlying Pt connections. IrOx nanotubes electrodeposited in this nanohole template are uniform in both size and shape. We randomly picked thirty nanotubes to measure their diameters and wall thickness by SEM line scans. Nanotube diameter is defined as the separation between the two intensity peaks; and wall thickness is defined as the full width at half maximum at each peak. The average nanotube radius is 90.7±1.4 nm and the average wall thickness is 39.8±3.0 nm (n=30) for an electron beam lithography write radius of 70 nm and exposure dose of 250 μC/cm$^2$ at 20 kV. By writing other diameters, we can fabricate IrOx nanotubes of different diameters.

Relationship Between Recording Amplitude and Pore Conductance

The simplified equivalent circuit model in FIG. 16 shows that the recorded signal $V_{rec}=V_{in}R_{seal}/(R_{seal}+R_{access})$, where $V_{in}$ is the membrane potential, $R_{seal}$ the sealing resistance, and Raccess the access resistance between the nanotube electrodes and the cell interior. In most of our recordings, Raccess>>$R_{seal}$ (~100 MΩ) because the gap between the plasma membrane and the electrode is larger than the size of the electroporated holes. Thus $V_{rec}=V_{in}R_{seal}/R_{access}$ and our recorded signal is only a fraction of the actual membrane potential. Since the access resistance is governed by the pores created by electroporation, we substitute the pore conductance $g_{pores}=R_{access}^{-1}$ to obtain $V_{rec}=V_{in}R_{seal}g_{pores}$ and $\Delta V_{rec}=V_{in}R_{seal}\Delta g_{pores}$. Therefore, the change in the recorded signal amplitude is linearly proportional to the total conductance of the pores. In the special case that all pores are of the same size, $g_{pores}=Ng_0$ and $\Delta V_{rec}=V_{in}R_{seal}g_0\Delta N$, where N is the number of pores and g0 is the conductance of a single pore.

Comparison Between IrOx Nanotube and Pt Nanopillar Electrodes

We previously fabricated electrodes consisted of three-by-three arrays of Pt nanopillar using focused ion beam Pt deposition. The nanopillars were of 150 nm in diameter and 1.5-2 µm in height, which is different from the IrOx nanotubes of 180 nm in diameter and ~500 nm in height presented in this paper. Although both types of electrode are capable of recording action potentials of similar amplitudes, the Pt nanopillar electrodes achieve intracellular access for only less than two minutes, similar to that of the electrodeposited Au nanopillar electrodes. The IrOx nanotube electrodes possess 1-2 orders of magnitudes longer intracellular access duration.

While certain embodiments of the invention have been illustrated and described, it will be appreciated that various changes can be made therein without departing from the spirit and scope of the invention.

What is claimed is:

1. A method for measuring membrane potentials from a cell using an electrode device, the method comprising:
   placing an electrode array in contact with cell membrane of the cell such that a nano-scale electrode of the electrode array is engulfed by a portion of the membrane, the electrode array comprising a plurality of nano-scale electrodes that are vertically aligned in the electrode array;
   recording extracellular signals of the cell using the nano-scale electrode, the extracellular signals indicating at least one action potential of the cell;
   electroporating, using the nano-scale electrode, the cell to increase the permeability of the portion of the cell membrane engulfing the nano-scale electrode such that intracellular signals of the cell are recorded by the nano-scale electrode in response to the electroporation; and
   recording the intracellular signals of the cell using the nano-scale electrode, the intracellular signals indicating one or more action potentials of the cell, wherein the electrode device comprising:
   a substrate patterned with a plurality of metal pads;
   a plurality of electrode arrays, each electrode array attached to the substrate above a metal pad and electrically connected to the metal pad; and
   a chamber surrounding the plurality of nano-scale electrodes.

2. The method of claim 1, wherein the cell is selected from the group consisting of a neuron, a muscle cell, and an endocrine cell.

3. The method of claim 1, further comprising:
   switching between extracellular and intracellular recording by nano-scale electroporation via the nano-scale electrode.

4. The method of claim 1, wherein the permeability of the cell membrane is permeability of the cell membrane to ions or electrons.

5. The method of claim 4, wherein electroporation is repeated for 20 pulses over a period of 1 second.

* * * * *